(12) United States Patent
Li et al.

(10) Patent No.: US 12,410,474 B2
(45) Date of Patent: *Sep. 9, 2025

(54) METHODS, KITS, AND DEVICES FOR DIAGNOSING, PROGNOSING, AND TREATING PSYCHIATRIC DISORDERS IN A PATIENT

(71) Applicant: Northwestern University, Evanston, IL (US)

(72) Inventors: Jiang Li, Chicago, IL (US); Herbert Y. Meltzer, Chicago, IL (US)

(73) Assignee: Northwestern University, Evanston, IL (US)

( * ) Notice: Subject to any disclaimer, the term of this patent is extended or adjusted under 35 U.S.C. 154(b) by 840 days.

This patent is subject to a terminal disclaimer.

(21) Appl. No.: 17/526,498

(22) Filed: Nov. 15, 2021

(65) Prior Publication Data

US 2022/0177970 A1 Jun. 9, 2022

Related U.S. Application Data

(63) Continuation of application No. 14/841,043, filed on Aug. 31, 2015, now Pat. No. 11,174,514.

(60) Provisional application No. 62/043,937, filed on Aug. 29, 2014.

(51) Int. Cl.
| | |
|---|---|
| *C12Q 1/68* | (2018.01) |
| *A61K 31/454* | (2006.01) |
| *A61K 31/519* | (2006.01) |
| *A61K 31/551* | (2006.01) |
| *A61K 31/5513* | (2006.01) |
| *C07H 21/04* | (2006.01) |
| *C12Q 1/6883* | (2018.01) |

(52) U.S. Cl.
CPC .......... *C12Q 1/6883* (2013.01); *A61K 31/454* (2013.01); *A61K 31/519* (2013.01); *A61K 31/551* (2013.01); *A61K 31/5513* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS 11,174,514 B2 * 11/2021 Li .................. A61K 31/519

OTHER PUBLICATIONS

De Luca et al. (Human Psychopharmacology, vol. 22, pp. 463-467, 2007) (Year: 2007).*
Gunes et al. (Eur. J. Clin Pharmacol, vol. 64, pp. 477-482, 2008). (Year: 2008).*
Liu et al. (Pharmacogenomics, vol. 11, No. 5, pp. 685-692, 2010). (Year: 2010).*
Barnes NM, Sharp T (1999) A review of central 5-HT receptors and their function. Neuropharmacology 38: 1083-1152.
Berg KA, Clarke WP, Cunningham KA, Spampinato U (2008) Fine-tuning serotonin2c receptor function in the brain: molecular and functional implications. Neuropharmacology 55: 969-976.
Boothman L, Raley J, Denk F, Hirani E, Sharp T (2006) In vivo evidence that 5-HT(2C) receptors inhibit 5-HT neuronal activity via a GABAergic mechanism. Br J Pharmacol 149: 861-869.
Brummett BH, Babyak MA, Jiang R, Shah SH, Becker RC, et al. (2013) A functional polymorphism in the 5HTR2C gene associated with stress responses also predicts incident cardiovascular events. PLoS One 8: e82781.
Buckland PR, Hoogendoorn B, Guy CA, Smith SK, Coleman SL, et al. (2005) Low gene expression conferred by association of an allele of the 5-HT2C receptor gene with antipsychotic-induced weight gain. Am J Psychiatry 162: 613-615.
Colantuoni C, Lipska BK, Ye T, Hyde TM, Tao R, et al. (2011) Temporal dynamics and genetic control of transcription in the human prefrontal cortex. Nature 478: 519-523.
Covell NH, Weissman EM, Essock SM (2004) Weight gain with clozapine compared to first generation antipsychotic medications. Schizophr Bull 30: 229-240.
Dunlop J, Watts SW, Barrett JE, Coupet J, Harrison B, et al. (2011) Characterization of vabicaserin (SCA-136), a selective 5-hydroxytryptamine 2C receptor agonist. J Pharmacol Exp Ther 337: 673-680.
Fentress HM, Grinde E, Mazurkiewicz JE, Backstrom JR, Herrick-Davis K, et al. (2005) Pharmacological properties of the Cys23Ser single nucleotide polymorphism in human 5-HT2C receptor isoforms. Pharmacogenomics J 5: 244-254.
Gavarini S, Becamel C, Altier C, Lory P, Poncet J, et al. (2006) Opposite effects of PSD-95 and MPP3 Pdz proteins on serotonin 5-hydroxytryptamine2C receptor desensitization and membrane stability. Mol Biol Cell 17: 4619-4631.
Gurevich I, Tamir H, Arango V, Dwork AJ, Mann JJ, et al. (2002) Altered editing of serotonin 2C receptor pre-mRNA in the prefrontal cortex of depressed suicide victims. Neuron 34: 349-356.
Hernando-Herraez I, Prado-Martinez J, Garg P, Fernandez-Callejo M, Heyn H, et al. (2013) Dynamics of DNA methylation in recent human and great ape evolution. PLoS Genet 9: e1003763.
Holmes C, Arranz MJ, Powell JF, Collier DA, Lovestone S (1998) 5-HT2A and 5-HT2C receptor polymorphisms and psychopathology in late onset Alzheimer's disease. Hum Mol Genet 7: 1507-1509.

(Continued)

*Primary Examiner* — Jeanine A Goldberg
(74) *Attorney, Agent, or Firm* — Quarles & Brady LLP

(57) ABSTRACT

Disclosed are methods, kits, and devices for diagnosing and treating psychiatric disorders and the symptoms thereof. The methods, kits, and devices relate to identifying genetic markers that may be utilized to diagnose and/or prognose a patient and treat the diagnosed and/or prognosed patient by administering a drug the patient based on the genetic marker having been identified. Genetic markers identified in the methods may include HTR2C polymorphisms such as a polymorphism resulting in a Cys23Ser amino acid substitution, an rs3813929 (-759C/T) polymorphism, and an rs518147 (-697G/C) polymorphism).

8 Claims, 3 Drawing Sheets

Specification includes a Sequence Listing.

(56) References Cited

OTHER PUBLICATIONS

Iwamoto K, Kakiuchi C, Bundo M, Ikeda K, Kato T (2004) Molecular characterization of bipolar disorder by comparing gene expression profiles of postmortem brains of major mental disorders. Mol Psychiatry 9: 406-416.

Iwamoto K, Bundo M, Kato T (2009) Serotonin receptor 2C and mental disorders: genetic, expression and RNA editing studies. RNA Biol 6: 248-253.

Jentsch JD, Roth RH (1999) The neuropsychopharmacology of phencyclidine: from NMDA receptor hypofunction to the dopamine hypothesis of schizophrenia. Neuropsychopharmacology 20: 201-225.

Kay SR, Fiszbein A, Opler LA (1987) The positive and negative syndrome scale (PANSS) for schizophrenia. Schizophr Bull 13: 261-276.

Kirchheiner J, Nickchen K, Bauer M, Wong ML, Licinio J, et al. (2004) Pharmacogenetics of antidepressants and antipsychotics: the contribution of allelic variations to the phenotype of drug response. Mol Psychiatry 9: 442-473.

Kroeze WK, Hufeisen SJ, Popadak BA, Renock SM, Steinberg S, et al. (2003) H1-histamine receptor affinity predicts short-term weight gain for typical and atypical antipsychotic drugs. Neuropsychopharmacology 28: 519-526.

Labasque M, Reiter E, Becamel C, Bockaert J, Marin P (2008) Physical interaction of calmodulin with the 5-hydroxytryptamine2C receptor C-terminus is essential for G protein-independent, arrestin-dependent receptor signaling. Mol Biol Cell 19: 4640-4650.

Lerer B, Macciardi F, Segman RH, Adolfsson R, Blackwood D, et al. (2001) Variability of 5-HT2C receptor cys23ser polymorphism among European populations and vulnerability to affective disorder. Mol Psychiatry 6: 579-585.

Marquis KL, Sabb AL, Logue SF, Brennan JA, Piesla MJ, et al. (2007) WAY-163909 [(7bR, 10aR)-1,2,3,4,8,9,10,10a-octahydro-7bH-cyclopenta-[b][1,4]diazepino[6,7, 1hi ]indole]: A novel 5-hydroxytryptamine 2C receptor-selective agonist with preclinical antipsychotic-like activity. J Pharmacol Exp Ther 320: 486-496.

Masellis M, Basile V, Meltzer HY, Lieberman JA, Sevy S, et al. (1998) Serotonin subtype 2 receptor genes and clinical response to clozapine in schizophrenia patients. Neuropsychopharmacology 19: 123-132.

Morabito MV, Emeson RB (2009) RNA editing as a therapeutic target for CNS disorders. Neuropsychopharmacology 34: 246.

Need AC, Keefe RS, Ge D, Grossman I, Dickson S, et al. (2009) Pharmacogenetics of antipsychotic response in the CATIE trial: a candidate gene analysis. Eur J Hum Genet 17: 946-957.

Niswender CM, Herrick-Davis K, Dilley GE, Meltzer HY, Overholser JC, et al. (2001) RNA editing of the human serotonin 5-HT2C receptor. alterations in suicide and implications for serotonergic pharmacotherapy. Neuropsychopharmacology 24: 478-491.

Numata S, Ye T, Hyde TM, Guitart-Navarro X, Tao R, et al. (2012) DNA methylation signatures in development and aging of the human prefrontal cortex. Am J Hum Genet 90: 260-272.

Okada M, Northup JK, Ozaki N, Russell JT, Linnoila M, et al. (2004) Modification of human 5-HT(2C) receptor function by Cys23Ser, an abundant, naturally occurring amino-acid substitution. Mol Psychiatry 9: 55-64.

Overall JE, Gorham DR (1962) The Brief Psychiatric Rating-Scale. Psychological Reports 10: 799-812.

Purcell S, Neale B, Todd-Brown K, Thomas L, Ferreira MA, et al. (2007) PLINK: a tool set for whole-genome association and population-based linkage analyses. Am J Hum Genet 81: 559-575.

Rauser L, Savage JE, Meltzer HY, Roth BL (2001) Inverse agonist actions of typical and atypical antipsychotic drugs at the human 5-hydroxytryptamine(2C) receptor. J Pharmacol Exp Ther 299: 83-89.

Segman RH, Ebstein RP, Heresco-Levy U, Gorfine M, Avnon M, et al. (1997) Schizophrenia, chronic hospitalization and the 5-HT2C receptor gene. Psychiatr Genet 7: 75-78.

Sodhi MS, Burnet PW, Makoff AJ, Kerwin RW, Harrison PJ (2001) RNA editing of the 5-HT(2C) receptor is reduced in schizophrenia. Mol Psychiatry 6: 373-379.

Yuan X, Yamada K, Ishiyama-Shigemoto S, Koyama W, Nonaka K (2000) Identification of polymorphic loci in the promoter region of the serotonin 5-HT2C receptor gene and their association with obesity and type II diabetes. Diabetologia 43: 373-376.

Lieberman, et al., "Effectiveness of Antipsychotic Drigs in Patients with Chromic Schizophrenia", The New England Journal of Medicine, Sep. 22, 2005; 353:1209-1223. Retrieved from the internet at: https://www.nejm.org/doi/full/10.1056/NEJMoa051688 on Jan. 10, 2020, 25 pages.

Abi-Dargham A, van de Giessen E, Slifstein M, Kegeles LS, Laruelle M (2009) Baseline and amphetamine-stimulated dopamine activity are related in drug-naive schizophrenic subjects. Biol Psychiatry 65: 1091-1093.

Arranz MJ, Munro J, Birkett J, Bolonna A, Mancama D, et al. (2000) Pharmacogenetic prediction of clozapine response. Lancet 355: 1615-1616.

Assal F, Alarcon M, Solomon EC, Masterman D, Geschwind DH, et al. (2004) Association of the serotonin transporter and receptor gene polymorphisms in neuropsychiatric symptoms in Alzheimer disease. Arch Neurol 61: 1249-1253.

Bundo M, Iwamoto K, Yamada K, Yoshikawa T, Kato T (2010) Mutation screening and assessment of the effect of genetic variations on expression and RNA editing of serotonin receptor 2C in the human brain. Psychiatry Clin Neurosci 64: 57-61.

Burns CM, Chu H, Rueter SM, Hutchinson LK, Canton H, et al. (1997) Regulation of serotonin-2C receptor G-protein coupling by RNA editing. Nature 387: 303-308.

Calcagno E, Carli M, Baviera M, Invernizzi RW (2009) Endogenous serotonin and serotonin2C receptors are involved in the ability of M100907 to suppress cortical glutamate release induced by NMDA receptor blockade. J Neurochem 108: 521-532.

Castensson A, Emilsson L, Sundberg R, Jazin E (2003) Decrease of serotonin receptor 2C in schizophrenia brains identified by high-resolution mRNA expression analysis. Biol Psychiatry 54: 1212-1221.

Di Giovanni G, De Deurwaerdere P, Di Mascio M, Di Matteo V, Esposito E, et al. (1999) Selective blockade of serotonin-2C/2B receptors enhances mesolimbic and mesostriatal dopaminergic function: a combined in vivo electrophysiological and microdialysis study. Neuroscience 91: 587-597.

Endicott J, Spitzer RL (1978) A diagnostic interview: the schedule for affective disorders and schizophrenia. Arch Gen Psychiatry 35: 837-844.

Giorgetti M, Tecott LH (2004) Contributions of 5-HT(2C) receptors to multiple actions of central serotonin systems. Eur J Pharmacol 488: 1-9.

Gunes A, Dahl ML, Spina E, Scordo MG (2008) Further evidence for the association between 5-HT2C receptor gene polymorphisms and extrapyramidal side effects in male schizophrenic patients. Eur J Clin Pharmacol 64: 477-482.

Gutierrez B, Fananas L, Arranz MJ, Valles V, Guillamat R, et al. (1996) Allelic association analysis of the 5-HT2C receptor gene in bipolar affective disorder. Neurosci Lett 212: 65-67.

Guy W (1976) ECDEU Assessment Manual for Psychopharmacology—Revised. DHEW Publ No. ADM 76: 218-222.

Hill MJ, Reynolds GP (2011) Functional consequences of two HTR2C polymorphisms associated with antipsychotic-induced weight gain. Pharmacogenomics 12: 727-734.

Hsueh YP (2006) The role of the MAGUK protein CASK in neural development and synaptic function. Curr Med Chem 13: 1915-1927.

Ju X, Giotakis O, Li T, Karwautz A, Treasure J, et al. (2003) Association of the 5-HT2c gene with susceptibility and minimum body mass index in anorexia nervosa. Neuroreport 14: 781-783.

Kusumi M, Araki H, Ijiri T, Kowa H, Adachi Y, et al. (2004) Serotonin 2C receptor gene Cys23Ser polymorphism: a candidate genetic risk factor of migraine with aura in Japanese population. Acta Neurol Scand 109: 407-409.

(56) References Cited

OTHER PUBLICATIONS

Lappalainen J, Zhang L, Dean M, Oz M, Ozaki N, et al. (1995) Identification, expression, and pharmacology of a Cys23-Ser23 substitution in the human 5-HT2c receptor gene (HTR2C). Genomics 27: 274-279.

Laruelle M (1998) Imaging dopamine transmission in schizophrenia. A review and meta-analysis. Q J Nucl Med 42: 211-221.

Lindenmayer JP, Bernstein-Hyman R, Grochowski S (1994) A new five factor model of schizophrenia. Psychiatr Q 65: 299-322.

Lisman JE, Coyle JT, Green RW, Javitt DC, Benes FM, et al. (2008) Circuit-based framework for understanding neurotransmitter and risk gene interactions in schizophrenia. Trends Neurosci 31: 234-242.

Liu BC, Zhang J, Wang L, Li XW, Wang Y, et al. (2010) HTR2C promoter polymorphisms are associated with risperidone efficacy in Chinese female patients. Pharmacogenomics 11: 685-692.

Malhotra AK, Goldman D, Ozaki N, Rooney W, Clifton A, et al. (1996) Clozapine response and the 5HT2C Cys23Ser polymorphism. Neuroreport 7: 2100-2102.

Meltzer HY, Brennan MD, Woodward ND, Jayathilake K (2008) Association of Sult4A1 SNPs with psychopathology and cognition in patients with schizophrenia or schizoaffective disorder. Schizophr Res 106: 258-264.

Meltzer HY, Li Z, Kaneda Y, Ichikawa J (2003) Serotonin receptors: their key role in drugs to treat schizophrenia. Prog Neuropsychopharmacol Biol Psychiatry 27: 1159-1172.

Meltzer HY, Huang M (2008) In vivo actions of atypical antipsychotic drug on serotonergic and dopaminergic systems. Prog Brain Res 172: 177-197.

Mickey BJ, Sanford BJ, Love TM, Shen PH, Hodgkinson CA, et al. (2012) Striatal dopamine release and genetic variation of the serotonin 2C receptor in humans. J Neurosci 32: 9344-9350.

Murad I, Kremer I, Dobrusin M, Muhaheed M, Bannoura I, et al. (2001) A family-based study of the Cys23Ser 5HT2C serotonin receptor polymorphism in schizophrenia. Am J Med Genet 105: 236-238.

Pritchard AL, Harris J, Pritchard CW, Coates J, Haque S, et al. (2008) Role of 5HT 2A and 5HT 2C polymorphisms in behavioural and psychological symptoms of Alzheimer's disease. Neurobiol Aging 29: 341-347.

Reynolds GP, Yao Z, Zhang X, Sun J, Zhang Z (2005) Pharmacogenetics of treatment in first-episode schizophrenia: D3 and 5-HT2C receptor polymorphisms separately associate with positive and negative symptom response. Eur Neuropsychopharmacol 15: 143-151.

Rietschel M, Naber D, Fimmers R, Moller HJ, Propping P, et al. (1997) Efficacy and side-effects of clozapine not associated with variation in the 5-HT2C receptor. Neuroreport 8: 1999-2003.

Rushlow WJ, Seah C, Sutton LP, Bjelica A, Rajakumar N (2009) Antipsychotics affect multiple calcium calmodulin dependent proteins. Neuroscience 161: 877-886.

Sodhi MS, Arranz MJ, Curtis D, Ball DM, Sham P, et al. (1995) Association between clozapine response and allelic variation in the 5-HT2C receptor gene. Neuroreport 7: 169-172.

Vehof J, Burger H, Wilffert B, Al Hadithy A, Alizadeh BZ, et al. (2012) Clinical response to antipsychotic drug treatment: association study of polymorphisms in six candidate genes. Eur Neuropsychopharmacol 22: 625-631.

Walstab J, Steinhagen F, Bruss M, Gothert M, Bonisch H (2011) Differences between human wild-type and C23S variant 5-HT2C receptors in inverse agonist-induced resensitization. Pharmacol Rep 63: 45-53.

\* cited by examiner

SEQUENCE LISTING

```
<160> NUMBER OF SEQ ID NOS: 10

<210> SEQ ID NO 1
<211> LENGTH: 458
<212> TYPE: PRT
<213> ORGANISM: Homo sapiens

<400> SEQUENCE: 1

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile Ile
    50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140
```

```
Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205

Leu Asn Asp Pro Asn Phe Val Leu Ile Gly Ser Phe Val Ala Phe Phe
    210                 215                 220

Ile Pro Leu Thr Ile Met Val Ile Thr Tyr Cys Leu Thr Ile Tyr Val
225                 230                 235                 240

Leu Arg Arg Gln Ala Leu Met Leu Leu His Gly His Thr Glu Glu Pro
                245                 250                 255

Pro Gly Leu Ser Leu Asp Phe Leu Lys Cys Cys Lys Arg Asn Thr Ala
            260                 265                 270

Glu Glu Glu Asn Ser Ala Asn Pro Asn Gln Asp Gln Asn Ala Arg Arg
        275                 280                 285

Arg Lys Lys Lys Glu Arg Arg Pro Arg Gly Thr Met Gln Ala Ile Asn
    290                 295                 300

Asn Glu Arg Lys Ala Ser Lys Val Leu Gly Ile Val Phe Phe Val Phe
305                 310                 315                 320

Leu Ile Met Trp Cys Pro Phe Phe Ile Thr Asn Ile Leu Ser Val Leu
                325                 330                 335

Cys Glu Lys Ser Cys Asn Gln Lys Leu Met Glu Lys Leu Leu Asn Val
            340                 345                 350

Phe Val Trp Ile Gly Tyr Val Cys Ser Gly Ile Asn Pro Leu Val Tyr
        355                 360                 365

Thr Leu Phe Asn Lys Ile Tyr Arg Arg Ala Phe Ser Asn Tyr Leu Arg
    370                 375                 380

Cys Asn Tyr Lys Val Glu Lys Lys Pro Pro Val Arg Gln Ile Pro Arg
385                 390                 395                 400

Val Ala Ala Thr Ala Leu Ser Gly Arg Glu Leu Asn Val Asn Ile Tyr
                405                 410                 415

Arg His Thr Asn Glu Pro Val Ile Glu Lys Ala Ser Asp Asn Glu Pro
            420                 425                 430

Gly Ile Glu Met Gln Val Glu Asn Leu Glu Leu Pro Val Asn Pro Ser
        435                 440                 445

Ser Val Val Ser Glu Arg Ile Ser Ser Val
    450                 455

<210> SEQ ID NO 2
<211> LENGTH: 248
<212> TYPE: PRT
<213> ORGANISM: Homo sapiens

<400> SEQUENCE: 2

Met Val Asn Leu Arg Asn Ala Val His Ser Phe Leu Val His Leu Ile
1               5                   10                  15

Gly Leu Leu Val Trp Gln Cys Asp Ile Ser Val Ser Pro Val Ala Ala
            20                  25                  30

Ile Val Thr Asp Ile Phe Asn Thr Ser Asp Gly Gly Arg Phe Lys Phe
        35                  40                  45

Pro Asp Gly Val Gln Asn Trp Pro Ala Leu Ser Ile Val Ile Ile Ile
    50                  55                  60
```

```
Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Cys Ile Ser Ser Tyr Pro Cys Asp
145                 150                 155                 160

Trp Thr Glu Gly Arg Arg Lys Gly Val Arg Glu Gln His Asp Val Arg
                165                 170                 175

Ala Gln Arg Pro Lys Phe Arg Ser Tyr Trp Val Leu Arg Ser Phe Leu
            180                 185                 190

His Thr Ala Asp Asp Tyr Gly Asp Tyr Val Leu Pro Asp His Leu Arg
        195                 200                 205

Ser Ala Pro Thr Ser Phe Asp Val Thr Ala Arg Pro His Arg Gly Thr
    210                 215                 220

Ala Trp Thr Lys Ser Gly Phe Pro Glu Val Leu Gln Glu Glu Tyr Gly
225                 230                 235                 240

Arg Gly Arg Glu Leu Cys Lys Pro
                245

<210> SEQ ID NO 3
<211> LENGTH: 1377
<212> TYPE: DNA
<213> ORGANISM: Homo sapiens

<400> SEQUENCE: 3
atggtgaacc tgaggaatgc ggtgcattca ttccttgtgc acctaattgg cctattggtt      60
tggcaatgtg atatttctgt gagcccagta gcagctatag taactgacat tttcaatacc     120
tccgatggtg gacgcttcaa attcccagac ggggtacaaa actggccagc actttcaatc     180
gtcatcataa taatcatgac aataggtggc aacatccttg tgatcatggc agtaagcatg     240
gaaaagaaac tgcacaatgc caccaattac ttcttaatgt ccctagccat tgctgatatg     300
ctagtgggac tacttgtcat gcccctgtct ctcctggcaa tcctttatga ttatgtctgg     360
ccactaccta gatatttgtg cccgtctgg atttctttag atgttttatt ttcaacagcg     420
tccatcatgc acctctgcgc tatatcgctg atcggtatg tagcaatacg taatcctatt     480
gagcatagcc gtttcaattc gcggactaag gccatcatga gattgctat tgtttgggca     540 atttctatag gtgtatcagt tcctatccct gtgattggac tgagggacga agaaaaggtg     600
ttcgtgaaca cacgacgtg cgtgctcaac gacccaaatt tcgttcttat tgggtccttc     660
gtagctttct tcataccgct tacgattatg gtgattacgt attgcctgac catctacgtt     720
ctgcgccgac aagctttgat gttactgcac ggccacaccg aggaaccgcc tggactaagt     780
ctggatttcc tgaagtgctg caagaggaat acggccgagg aagagaactc tgcaaaccct     840
aaccaagacc agaacgcacg ccgaagaaag aagaaggaga cgtcctag gggcaccatg      900 caggctatca acaatgaaag aaaagcttcg aaagtccttg ggattgtttt ctttgtgttt     960
ctgatcatgt ggtgcccatt tttcattacc aatattctgt ctgttctttg tgagaagtcc    1020
```

| | |
|---|---|
| tgtaaccaaa agctcatgga aaagcttctg aatgtgtttg tttggattgg ctatgtttgt | 1080 |
| tcaggaatca atcctctggt gtatactctg ttcaacaaaa tttaccgaag ggcattctcc | 1140 |
| aactatttgc gttgcaatta aaggtagag aaaaagcctc ctgtcaggca gattccaaga | 1200 |
| gttgccgcca ctgctttgtc tgggaggag cttaatgtta acatttatcg gcataccaat | 1260 |
| gaaccggtga tcgagaaagc cagtgacaat gagcccggta tagagatgca agttgagaat | 1320 |
| ttagagttac cagtaaatcc ctccagtgtg gttagcgaaa ggattagcag tgtgtga | 1377 |

<210> SEQ ID NO 4
<211> LENGTH: 747
<212> TYPE: DNA
<213> ORGANISM: Homo sapiens

<400> SEQUENCE: 4

| | |
|---|---|
| atggtgaacc tgaggaatgc ggtgcattca ttccttgtgc acctaattgg cctattggtt | 60 |
| tggcaatgtg atatttctgt gagcccagta gcagctatag taactgacat tttcaatacc | 120 |
| tccgatggtg gacgcttcaa attcccagac ggggtacaaa actggccagc actttcaatc | 180 |
| gtcatcataa taatcatgac aataggtggc aacatccttg tgatcatggc agtaagcatg | 240 |
| gaaaagaaac tgcacaatgc caccaattac ttcttaatgt ccctagccat tgctgatatg | 300 |
| ctagtgggac tacttgtcat gccctgtct ctcctggcaa tcctttatga ttatgtctgg | 360 |
| ccactaccta gatatttgtg ccccgtctgg atttctttag atgttttatt ttcaacagcg | 420 |
| tccatcatgc acctctgcgc tatatcgctg gatcggtgta tcagttccta tcctgtgat | 480 |
| tggactgagg gacgaagaaa aggtgttcgt gaacaacacg acgtgcgtgc tcaacgaccc | 540 |
| aaatttcgtt cttattgggt ccttcgtagc tttcttcata ccgctgacga ttatggtgat | 600 |
| tacgtattgc ctgaccatct acgttctgcg ccgacaagct tgatgttac tgcacggcca | 660 |
| caccgaggaa ccgcctggac taagtctgga tttcctgaag tgctgcaaga ggaatacggc | 720 |
| cgaggaagag aactctgcaa accctaa | 747 |

<210> SEQ ID NO 5
<211> LENGTH: 1377
<212> TYPE: DNA
<213> ORGANISM: Homo sapiens

<400> SEQUENCE: 5

| | |
|---|---|
| atggtgaacc tgaggaatgc ggtgcattca ttccttgtgc acctaattgg cctattggtt | 60 |
| tggcaatctg atatttctgt gagcccagta gcagctatag taactgacat tttcaatacc | 120 |
| tccgatggtg gacgcttcaa attcccagac ggggtacaaa actggccagc actttcaatc | 180 |
| gtcatcataa taatcatgac aataggtggc aacatccttg tgatcatggc agtaagcatg | 240 |
| gaaaagaaac tgcacaatgc caccaattac ttcttaatgt ccctagccat tgctgatatg | 300 |
| ctagtgggac tacttgtcat gccctgtct ctcctggcaa tcctttatga ttatgtctgg | 360 |
| ccactaccta gatatttgtg ccccgtctgg atttctttag atgttttatt ttcaacagcg | 420 |
| tccatcatgc acctctgcgc tatatcgctg gatcggtatg tagcaatacg taatcctatt | 480 |
| gagcatagcc gtttcaattc gcggactaag gccatcatga agattgctat tgtttgggca | 540 |
| atttctatag gtgtatcagt tcctatccct gtgattggac tgagggacga agaaaaggtg | 600 |
| ttcgtgaaca acacgacgtg cgtgctcaac gacccaaatt tcgttcttat tgggtccttc | 660 |
| gtagctttct tcataccgct gacgattatg gtgattacg attgcctgac catctacgtt | 720 |
| ctgcgccgac aagctttgat gttactgcac ggccacaccg aggaaccgcc tggactaagt | 780 |

```
ctggatttcc tgaagtgctg caagaggaat acggccgagg aagagaactc tgcaaaccct    840
aaccaagacc agaacgcacg ccgaagaaag aagaaggaga cgtcctag gggcaccatg     900 caggctatca acaatgaaag aaaagcttcg aaagtccttg ggattgtttt ctttgtgttt    960
ctgatcatgt ggtgcccatt tttcattacc aatattctgt ctgttctttg tgagaagtcc   1020
tgtaaccaaa agctcatgga aaagcttctg aatgtgtttg tttggattgg ctatgtttgt   1080
tcaggaatca atcctctggt gtatactctg ttcaacaaaa tttaccgaag gcattctcc    1140 aactatttgc gttgcaatta taaggtagag aaaaagcctc ctgtcaggca gattccaaga   1200
gttgccgcca ctgctttgtc tgggagggag cttaatgtta acatttatcg cataccaat    1260 gaaccggtga tcgagaaagc cagtgacaat gagcccggta tagagatgca agttgagaat   1320
ttagagttac cagtaaatcc ctccagtgtg gttagcgaaa ggattagcag tgtgtga      1377
```

```
<210> SEQ ID NO 6
<211> LENGTH: 720
<212> TYPE: DNA
<213> ORGANISM: Homo sapiens

<400> SEQUENCE: 6
atggtgaacc tgaggaatgc ggtgcattca ttccttgtgc acctaattgg cctattggtt     60
tggcaatctg atatttctgt gagcccagta gcagctatag taactgacat tttcaatacc    120
tccgatggtg gacgcttcaa attcccagac ggggtacaaa actggccagc actttcaatc    180
gtcatcataa taatcatgac aataggtggc aacatccttg tgatcatggc agtaagcatg    240
gaaaagaaac tgcacaatgc caccaattac ttcttaatgt ccctagccat tgctgatatg    300
ctagtgggac tacttgtcat gcccctgtct ctcctggcaa tcctttatga ttatgtctgg    360
ccactaccta gatatttgtg cccgtctgg atttctttag atgttttatt ttcaacagcg    420
tccatcatgc acctctgcgc tatatcgctg atcggtgta tcagttccta tccctgtgat    480
tggactgagg gacgaagaaa aggtgttcgt gaacaacacg acgtgcgtgc tcaacgaccc    540
aaatttcgtt cttattgggt ccttcgtagc ttttcttcata ccgctgacga ttatggtgat    600
tacgtattgc ctgaccatct acgttctgcg ccgacaagct tgatgttac tgcacggcca    660 caccgaggaa ccgcctggac taagtctgga tttcctgaag tgctgcaaga ggaatacggc    720
```

```
<210> SEQ ID NO 7
<211> LENGTH: 60
<212> TYPE: DNA
<213> ORGANISM: Homo sapiens

<400> SEQUENCE: 7
attggctgct cttggctcct cccctcatcc cgcttttggc ccaagagcgt ggtgcagatt     60
```

```
<210> SEQ ID NO 8
<211> LENGTH: 60
<212> TYPE: DNA
<213> ORGANISM: Homo sapiens

<400> SEQUENCE: 8
attggctgct cttggctcct cccctcatcc tgcttttggc ccaagagcgt ggtgcagatt     60
```

```
<210> SEQ ID NO 9
<211> LENGTH: 60
<212> TYPE: DNA
<213> ORGANISM: Homo sapiens
```

```
<400> SEQUENCE: 9
atcggtgcat ctgaggaagg aagcgtcctc ggcaagcacc agagcgccta cctcgcgcgg    60

<210> SEQ ID NO 10
<211> LENGTH: 60
<212> TYPE: DNA
<213> ORGANISM: Homo sapiens

<400> SEQUENCE: 10
atcggtgcat ctgaggaagg aagcgtcctc gccaagcacc agagcgccta cctcgcgcgg    60
```

METHODS, KITS, AND DEVICES FOR DIAGNOSING, PROGNOSING, AND TREATING PSYCHIATRIC DISORDERS IN A PATIENT

CROSS-REFERENCE TO RELATED PATENT APPLICATIONS

The present application is a continuation of U.S. patent application Ser. No. 14/841,043, filed Aug. 31, 2015, which claims the benefit of priority under 35 U.S.C. § 119 (e) to U.S. Provisional Patent Application No. 62/043,937, filed on Aug. 29, 2014, the contents of which are incorporated herein by reference in their entirety.

SEQUENCE LISTING

A Sequence Listing accompanies this application and is submitted as an ASCII text file of the sequence listing named "2015-08-31_5369-00111_sequence_listing.txt" which is 12,873 bytes in size and was created on Nov. 15, 2021. The sequence listing is electronically submitted via EFS-Web with the application and is incorporated herein by reference in its entirety.

BACKGROUND

The invention relates to methods for diagnosing and treating psychiatric disorders. In particular, the intention relates to methods for identifying genetic markers that are associated with treatment response for psychiatric disorders in a patient and administering drugs to the patient based on identifying the genetic markers. The genetic markers may include polymorphisms such as single nucleotide polymorphisms (SNPs) and the drugs may include typical and atypical antipsychotic drugs (APDs).

SUMMARY

Disclosed are methods, kits, and devices for diagnosing and treating psychiatric disorders and the symptoms thereof. The methods, kits, and devices relate to identifying genetic markers that may be utilized to diagnose and/or prognose a patient and treat the diagnosed and/or prognosed patient by administering a drug to the patient based on the genetic marker having been identified. Genetic markers identified in the methods may include HTR2C polymorphisms. Based on the polymorphism being identified in the patient, the patient may be identified as having responsiveness to an antipsychotic drug (APD), such as a typical APD or an atypical APD. As such, the patient may be treated by administering the APD to treat the psychiatric disorder and/or the symptoms thereof after the HTR2C polymorphism has been identified.

In some embodiments, the disclosed methods related to methods for treating a psychiatric disorder or the symptoms thereof in a patient. The disclosed methods may comprise the following steps: (a) determining whether the patient has a HTR2C polymorphism, or receiving the results of test indicating that a patient has a HTR2C polymorphism; and (b) administering an antipsychotic drug (APD) if the patient has the HTR2C polymorphism. In the disclosed methods, the psychiatric disorder may include, but is not limited to schizophrenia (e.g., schizophrenia characterized by positive symptoms, negative symptoms, and/or cognitive symptoms), bipolar disorder, and psychiatric depression with psychotic features. Suitable HTR2C polymorphisms detected in the methods or indicated in the test results utilized in the methods may include, but are not limited to a polymorphism resulting in a Cys23Ser amino acid substitution (e.g., a UGC←→UCC transversion or a UGU←→UCU transversion), an rs3813929 (-759C/T) polymorphism, and an rs518147 (-697G/C) polymorphism.

In some embodiments of the disclosed methods, the patient may have undergone treatment prior to the disclosed methods being performed and the patient may have been diagnosed with a treatment resistant psychiatric disorder prior to the method being performed. Accordingly, the methods contemplated herein include methods for determining treatment responsiveness and treating patients with the appropriate APD.

The presently disclosed methods relate to HTR2C polymorphisms, which may include but are not limited to a polymorphism resulting in a Cys23Ser amino acid substitution (e.g., a UGC←→UCC transversion or a UGU←→UCU transversion), an rs3813929 (-759C/T) polymorphism, and an rs518147 (-697G/C) polymorphism. The disclosed methods may include determining or detecting a nucleotide sequence associated with HTR2C polymorphisms. In some embodiments, the methods including determining whether the patient has one or more HTR2C polymorphisms by sequencing a nucleic acid sample obtained from the patient. In other embodiments, the methods may include determining whether the patient has one ore more HTR2C polymorphisms by treating a nucleic acid sample obtained from the patient with a nucleic acid probe (e.g. a probe that hybridizes specifically to a nucleic acid sequence comprising the HTR2C polymorphic allele). The methods may include determining whether the patient is homozygous or heterozygous for a HTR2C polymorphic allele. Further, the methods may include administering a pharmaceutical agent if the patient is found to be homozygous or heterozygous for the HTR2C polymorphic allele.

The disclosed methods typically include treating a patient based on the genotype of the patient with respect to the HTR2C polymorphism, which may include but are not limited to a polymorphism resulting in a Cys23Ser amino acid substitution, an rs3813929 (-759C/T) polymorphism, and an rs518147 (-697G/C) polymorphism. For example, the methods typically include administering a pharmaceutical agent to the patient if the patient is homozygous or heterozygous for a HTR2C polymorphic allele.

Also disclosed herein are kits and devices for performing the disclosed methods, and systems comprising the disclosed kits and devices. For example, the disclosed kits and devices may include and/or utilize reagents for diagnosing, prognosing, and/or treating a psychiatric disease or disorder or the symptoms thereof in a patient. The presently disclosed kits and devices may include and/or utilize reagents such as: (a) reagents for detecting the genotype of a patient in regard to a HTR2C polymorphism (e.g., where the patient has a polymorphism resulting in a Cys23 Ser amino acid substitution, where the patient is homozygous or heterozygous for the rs3813929 (-759C/T) polymorphic allele, and/or where the patient is homozygous or heterozygous for the rs518147 (-697G/C) polymorphic allele). The kits and devices may include and/or utilize reagents for amplifying and or sequencing nucleic acid comprising one or more HTR2C polymorphisms and/or reagents for probing nucleic acid comprising one or more HTR2C polymorphisms; and optionally (b) a pharmaceutical agent comprising an atypical drug for treating a psychiatric disease or disorder (e.g., clozapine, olanzapine, risperidone, and sertindole). The reagents in the kit may include nucleic acid reagents (e.g., primers and/or probes that hybridize to the HTR2C gene and that may be utilized to amplify, sequence, and/or probe the HTR2C gene or an RNA expressed from the HTR2C gene) and non-nucleic acid reagents (e.g., polymerases and buffers). The pharmaceutical agent of the kits and devices may include a typical or atypical APD for treating the psychiatric disease or disorder formulated for administration to the patient.

DETAILED DESCRIPTION

Figure 1:
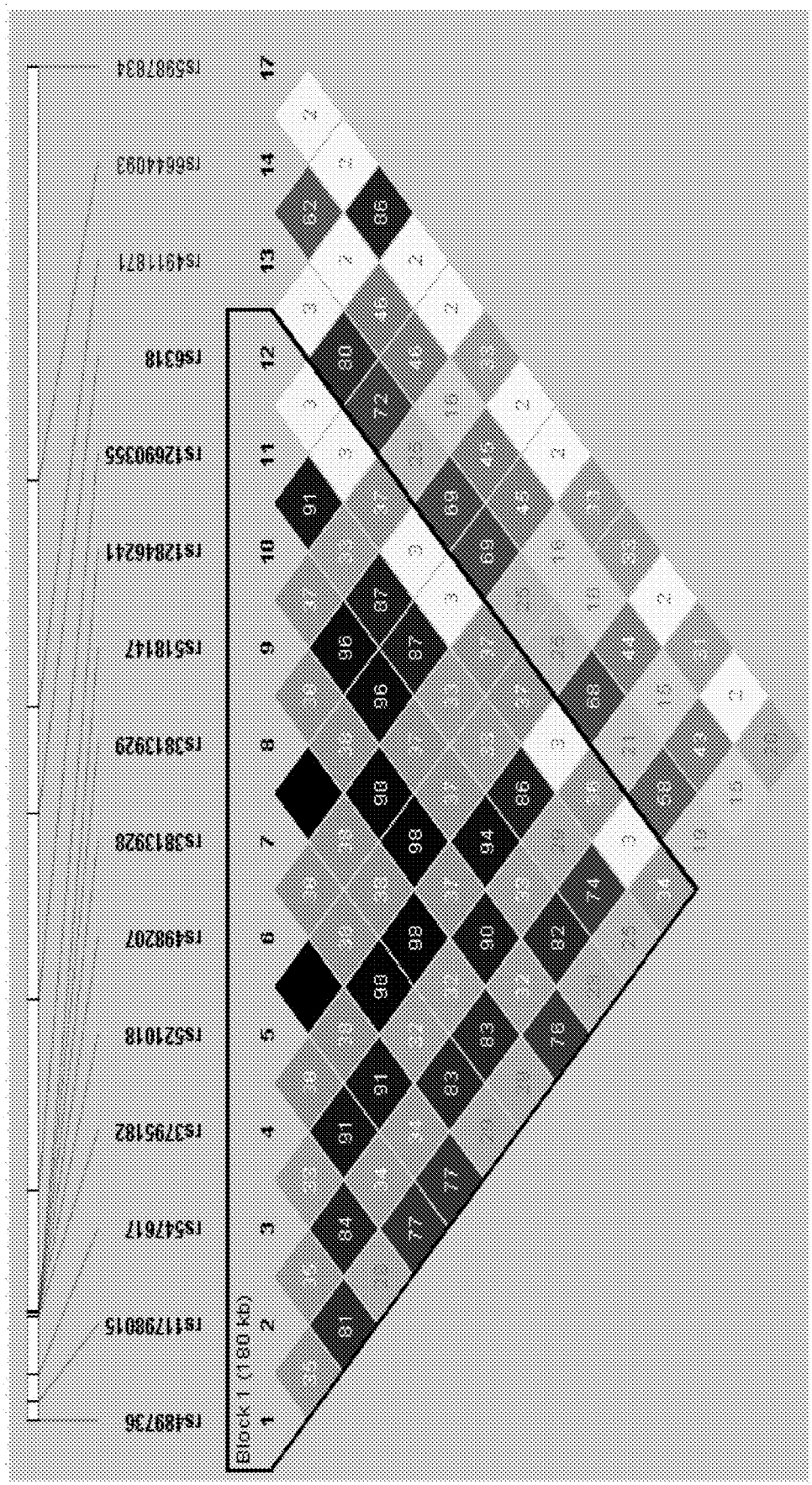
FIG. 1. Haploview plot of SNPs in Caucasians from 1000 genome data.

Disclosed are methods, kits, and devices for diagnosing and treating psychiatric disorders and the symptoms thereof. The methods, kits, and devices are described herein using several definitions, as set forth below and throughout the application.

As used in this specification and the claims, the singular forms "a," "an," and "the" include plural forms unless the context clearly dictates otherwise. For example, "a polymorphism" should be interpreted to mean "one or more polymorphisms" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods, kits, and devices relate to identifying genetic markers that may be utilized to diagnose and/or prognose a patient, and optionally treat the diagnosed and/or prognosed patient by administering a drug to the patient based on the genetic marker having been identified.

As used herein, the term "patient," which may be used interchangeably with the terms "subject" or "individual," refers to one who receives medical care, attention or treatment and may encompass a human patient. As used herein, the term "patient" is meant to encompass a person who has a psychiatric disorder or is at risk for developing a psychiatric disorder, which includes but is not limited to schizophrenia, bipolar disorder, and psychotic depression (e.g., depression with psychotic features). For example, the term "patient" is meant to encompass a person at risk for developing schizophrenia or a person diagnosed with schizophrenia (e.g., a person who may be symptomatic for schizophrenia but who has not yet been diagnosed). As used herein, "schizophrenia" may include schizophrenia characterized by positive symptoms, negative symptoms, cognitive symptoms, or any combination thereof. The term "patient" also is meant to encompass a person at risk for developing bipolar disorder or a person diagnosed with bipolar disorder (e.g., a person who may be symptomatic for bipolar disorder but who has not yet been diagnosed). The term "patient" further is meant to encompass a person at risk for developing depression (e.g., depression with psychotic features). As such, the term "patient" further is meant to encompass a person at risk for developing depression with psychotic features or a person diagnosed with depression with psychotic features (e.g., a person who may be symptomatic for depression with psychotic features but who has not yet been diagnosed).

The disclosed methods may include: (a) detecting a HTR2C polymorphism in a nucleic acid sample from a patient having a psychiatric disease or disorder; and (b) administering an antipsychotic drug (APD) to the patient after the HTRC2C polymorphism is detected. In some embodiments, the HTR2C polymorphism may be detected by a step that includes amplifying at least a portion of the HTR2C gene from the nucleic acid sample and detecting the HTR2C polymorphism in the amplified portion. In further embodiments, the HTR2C polymorphism may be detected by a step that includes sequencing at least a portion of the HTR2C gene from the nucleic acid sample or from an amplicon obtained by amplifying at least a portion of the HTR2C gene from the nucleic acid sample. In even further embodiments, the HTR2C polymorphism may be detected by a step that includes contacting nucleic acid comprising the HTR2C polymorphism with a nucleic acid probe that hybridizes specifically to nucleic acid comprising the HTR2C polymorphism.

Genetic markers identified in the methods typically include HTR2C polymorphisms. Exemplary HTR2C polymorphisms detected in the disclosed methods may include, but are not limited to a polymorphism resulting in a Cys23 Ser amino acid substitution, an rs3813929 (-759C/T) polymorphism, and an rs518147 (-697G/C) polymorphism. The disclosed methods may include determining whether a patient is homozygous or heterozygous for the HTR2C polymorphism (e.g., by determining whether a nucleic acid sample from the patient is homozygous or heterozygous for the HTR2C polymorphism). Methods, compositions, and kits for diagnosing, prognosing, and treating psychiatric disorders that include steps of detecting genetic polymorphisms also are disclosed in U.S. Published Application No. 2015/0099741, the content of which is incorporate herein by reference in its entirety.

As used herein, "HTR2C" refers to "5-hydroxytryptamine receptor 2C isoform." Gene information for HTR2C is provided at the NCBI database as follows: "HTR2C 5-hydroxytryptamine (serotonin) receptor 2C, G protein-coupled [Homo sapiens (human)] Gene ID: 3358." The HTR2C isoform "a precursor" is a 458 amino acid polypeptide, the amino acid sequence of which is provided at the NCBI database under Accession No. NP_001243689 (SEQ ID NO:1). The HTR2C isoform "b precursor" is a 248 amino acid polypeptide, the amino acid sequence of which is provided at the NCBI database under Accession No. NP_001243690 (SEQ ID NO:2). As used herein, a nucleic acid reagent that specifically hybridizes to HTR2C may include a nucleic acid reagent that specifically hybridizes to a polynucleotide that encodes the amino acid sequence of SEQ ID NO:1 or SEQ ID NO:2. For example, a nucleic acid reagent that specifically hybridizes to HTR2C may include a nucleic acid reagent that specifically hybridizes to the cDNA (or mRNA) encoding the HTR2C isoform "a precursor" (see SEQ ID NO:3 and NCBI database CCDS59174)) or to the cDNA (or mRNA) encoding the HTR2C isoform "b precursor" (see SEQ ID NO:4 and NCBI database CCDS14564). A nucleic acid reagent that specifically hybridizes to HTR2C may include a nucleic acid reagent that specifically hybridizes to a portion of the HTR2C gene comprising a mutation resulting in a Cys23Ser mutation (e.g., a portion of SEQ ID NO:5 or SEQ ID NO:6). A nucleic acid reagent that specifically hybridizes to HTR2C may include a nucleic acid reagent that specifically hybridizes to a portion of the HTR2C gene comprising the rs3813929 SNP (e.g., a portion of SEQ ID NO:7 or 8). A nucleic acid reagent that specifically hybridizes to HTR2C may include a nucleic acid reagent that specifically hybridizes to a portion of the HTR2C gene comprising the rs3813929 SNP (e.g., a portion of SEQ ID NO:9 or 10).

The disclosed methods may include detecting a HTR2C polymorphism in a nucleic acid sample from a patient having a psychiatric disease or disorder. As used herein, a "psychiatric disease or disorder" may include, but is not limited to schizophrenia, bipolar disorder, and psychiatric depression.

Based on the HTR2C polymorphism being identified in the patient, the patient may be identified as having responsiveness to an antipsychotic drug (APD), such as a typical APD or an atypical APD. As such, the patient may be treated by administering the APD to treat the psychiatric disorder and/or the symptoms thereof after the HTR2C polymorphism has been identified.

Accordingly, the disclosed methods, kits, and devices optionally may utilize or include an antipsychotic drug (APD). Suitable APDs may include typical APDs and atypical APDs. APDs for use in the disclosed methods, kits, and devices, may include, but are not limited to Clozapine (Clozaril®), Benperidol (Anguil®, Benguil®, Frenactil®, Glianimon®), Bromperidol (Bromodol®, Impromen®), Droperidol (Droleptan®, Inapsine®), Haloperidol (Haldol®, Serenace®), Moperone (Luvatren®), Pipamperone (Dipiperon®, Piperonil®), Timiperone (Celmanil®, Tolopelon®), Diphenylbutylpiperidine, Fluspirilene (Imap®), Penfluridol (Semap®), Pimozide (Orap®), Acepromazine (Plegicil®), Chlorpromazine (Largactil®, Thorazine®), Cyamemazine (Tercian®), Dixyrazine (Esucos®), Fluphenazine (Modecate®, Permitil®, Prolixin®), Levomepromazine (Levinan®, Levoprome®, Nozinan®), Mesoridazine (Lidanil®, Serentil®), Perazine (Peragal®, Perazin®, Pernazinum®, Taxilan®), Pericyazine (Neulactil®, Neuleptil®), Perphenazine (Trilafon®), Pipotiazine (Lonseren®, Piportil®), Prochlorperazine (Compazine®), Promazine (Prozine®, Sparine®), Promethazine (Avomine®, Phenergan®), Prothipendyl (Dominal®), Thioproperazine (Majeptil®), Thioridazine (Aldazine®, Mellaril®, Melleril®), Trifluoperazine (Stelazine®), Triflupromazine (Vesprin®), Chlorprothixene (Cloxan®, Taractan®, Truxal®), Clopenthixol (Sordinol®), Flupentixol (Depixol®, Fluanxol®), Tiotixene (Navane®, Thixit®), Zuclopenthixol (Acuphase®, Cisordinol®, Clopixol®), Clotiapine (Entumine®, Etomine®, Etumine®), Loxapine (Adasuve®, Loxitane®), Prothipendyl (Dominal®), Carpipramine (Defekton®, Prazinil®), Clocapramine (Clofekton®, Padrasen®), Molindone (Moban®), Mosapramine (Cremin®), Sulpiride (Meresa®), Sultopride (Barnetil®, Topral®), Veralipride (Agreal®), Amisulpride (Solian®), Amoxapine (Asendin®), Aripiprazole (Abilify®), Asenapine (Saphris®, Sycrest®), Blonanserin (Lonasen®), Iloperidone (Fanapt®, Fanapta®, Zomaril®), Lurasidone (Latuda®), Melperone (Buronil®, Buronon®, Eunerpan®, Melpax®, Neuril®), Olanzapine (Zyprexa®), Paliperidone (Invega®), Perospirone (Lullan®), Quetiapine (Seroquel®), Remoxipride (Roxiam®), Risperidone (Risperdal®), Sertindole (Serdolect®, Serlect®), Trimipramine (Surmontil®), Ziprasidone (Geodon®, Zeldox®), and Zotepine (Lodopin®, Losizopilon®, Nipolept®, Setous®). In some embodiments, the APD is an atypical APD that is an inverse agonist of the HTR2C receptor (and optional that is an inverse agonist of the HTR2A receptor). For example, atypical APDs that are inverse agonists of the HTR2C receptor and the HTR2A receptor may include clozapine, olanzapine, risperidone, and sertindole.

The disclosed methods, kits, and devices may utilize or include a reagent that is utilized for detecting an HTR2C polymorphism. Suitable reagents may include nucleic acid reagents. For example, nucleic acid reagents may include reagents comprising a DNA oligonucleotide that hybridizes specifically to the HTR2C gene or that hybridizes specifically to a polymorphism in the HTR2C gene. In some embodiments, the methods, kits, and device may utilize or include nucleic acid reagents that comprise one or more primers for sequencing at least a portion of the HTR2C gene (e.g., where the portion of the HTR2C comprises a HTR2C polymorphism selected from the group consisting of a polymorphism resulting in a Cys23Ser amino acid substitution, an rs3813929 (-759C/T) polymorphism, and an rs518147 (-697G/C) polymorphism). In further embodiments, the methods, kits, and device may utilize or include nucleic acid reagents that comprise one or more primer pairs for amplifying at least a portion of the HTR2C gene (e.g., where the portion of the HTR2C gene comprises a HTR2C polymorphism selected from the group consisting of a polymorphism resulting in a Cys23 Ser amino acid substitution, an rs3813929 (-759C/T) polymorphism, and an rs518147 (-697G/C) polymorphism).

The disclosed kits and/or devices disclosed herein may be assembled into systems for performing the methods disclosed herein. Manual and/or automated systems comprising the contemplated kits and/or devices are contemplated herein.

As used herein the terms "diagnose" or "diagnosis" or "diagnosing" refer to distinguishing or identifying a disease, syndrome or condition or distinguishing or identifying a person having or at risk for developing a particular disease, syndrome or condition. As used herein the terms "prognose" or "prognosis" or "prognosing" refer to predicting an outcome of a disease, syndrome or condition. The methods contemplated herein include diagnosing a psychiatric disorder in a patient that is associated with a HTR2C polymorphism. The methods contemplated herein also include determining a prognosis for a patient having a psychiatric disorder that is associated with a HTR2C polymorphism.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration. In particular, the methods contemplated herein include treating a patient having or at risk for developing a psychiatric disorder that is associated with a HTR2C polymorphism.

The present methods may include detecting a HTR2C polymorphism in a patient sample (e.g., a sample comprising nucleic acid). The term "sample" or "patient sample" is meant to include biological samples such as tissues and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The detected HTR2C polymorphism is present in nucleic acid. The term "nucleic acid" or "nucleic acid sequence" refers to an oligonucleotide, nucleotide or polynucleotide, and fragments or portions thereof, which may be single or double stranded, and represents the sense or antisense strand. A nucleic acid may include DNA or RNA, and may be of natural or synthetic origin. For example, a nucleic acid may include mRNA or cDNA. Nucleic acid may include nucleic acid that has been amplified (e.g., using polymerase chain reaction). Nucleic acid may include genomic nucleic acid.

As used herein, the term "assay" or "assaying" means qualitative or quantitative analysis or testing.

As used herein the term "sequencing," as in determining the sequence of a polynucleotide, refers to methods that determine the base identity at multiple base positions or that determine the base identity at a single position.

The term "amplification" or "amplifying" refers to the production of additional copies of a nucleic acid sequence. Amplification is generally carried out using polymerase chain reaction (PCR) technologies known in the art.

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The present methods and kits may utilize or contain primers, probes, or both. The term "primer" refers to an oligonucleotide that hybridizes to a target nucleic acid and is capable of acting as a point of initiation of synthesis when placed under conditions in which primer extension is initiated (e.g., primer extension associated with an application such as PCR). For example, primers contemplated herein may hybridize to one or more polynucleotide sequences comprising the HTR2C polymorphisms disclosed herein. A "probe" refers to an oligonucleotide that interacts with a target nucleic acid via hybridization. A primer or probe may be fully complementary to a target nucleic acid sequence or partially complementary. The level of complementarity will depend on many factors based, in general, on the function of the primer or probe. For example, probes contemplated herein may hybridize to one or more polynucleotide sequences comprising the HTR2C polymorphisms disclosed herein. A primer or probe may specifically hybridize to a target nucleic acid (e.g., hybridize under stringent conditions as discussed herein). In particular, primers and probes contemplated herein may hybridize specifically to one or more polynucleotide sequences that comprise the HTR2C polymorphisms disclosed herein and may be utilized to distinguish a polynucleotide sequence comprising a minor allele from a polynucleotide sequence comprising the major allele.

An "oligonucleotide array" refers to a substrate comprising a plurality of oligonucleotide primers or probes. The arrays contemplated herein may be used to detect the HTR2C polymorphisms disclosed herein.

As used herein, the term "specific hybridization" indicates that two nucleic acid sequences share a high degree of complementarity. Specific hybridization complexes form under stringent annealing conditions and remain hybridized after any subsequent washing steps. Stringent conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, a "target nucleic acid" refers to a nucleic acid molecule containing a sequence that has at least partial complementarity with a probe oligonucleotide, a primer oligonucleotide, or both. A primer or probe may specifically hybridize to a target nucleic acid.

The present methods may be performed to detect the presence or absence of the disclosed HTR2C polymorphisms. Methods of determining the presence or absence of a HTR2C polymorphism may include a variety of steps known in the art, including one or more of the following steps: reverse transcribing mRNA that comprises the HTR2C polymorphism to cDNA, amplifying nucleic acid that comprises the HTR2C polymorphism (e.g., amplifying genomic DNA that comprises the HTR2C polymorphism), hybridizing a probe or a primer to nucleic acid that comprises the HTR2C polymorphisms (e.g., hybridizing a probe to mRNA, cDNA, or amplified genomic DNA that comprises the HTR2C polymorphism), and sequencing nucleic acid that comprises the HTR2C polymorphism (e.g., sequencing cDNA, genomic DNA, or amplified DNA that comprises the HTR2C polymorphism).

A "polymorphism" refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism (SNP) is the replacement of one nucleotide by another nucleotide at the polymorphic site. Deletion of a single nucleotide or insertion of a single nucleotide also gives rise to single nucleotide polymorphisms. "Single nucleotide polymorphism" preferably refers to a single nucleotide substitution. Typically, between different individuals, the polymorphic site can be occupied by two different nucleotides which results in two different alleles with the most common allele in the population (i.e., the ancestral allele) being referred to as the "major allele" and the less common allele in the population being referred to as the "minor allele." An individual may be homozygous or heterozygous for the major allele or the minor allele of the polymorphism. "Mutation" as utilized herein, is intended to encompass a single nucleotide substitution, which may be recognized as a single nucleotide polymorphism. Exemplary SNPs disclosed herein include rs3813929 (-759C/T), and rs518147 (-697G/C).

In the methods and kits, the minor allele and/or the major allele associated with a polymorphism may be detected. The methods may include and the kits and devices may be used for determining whether a patient is homozygous or heterozygous for a minor allele and/or major allele associated with a polymorphism (e.g., a SNP). The term "heterozygous" refers to having different alleles at one or more genetic loci in homologous chromosome segments. As used herein "heterozygous" may also refer to a sample, a cell, a cell population or a patient in which different alleles (e.g., major or minor alleles of SNPs) at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, the term "homozygous" refers to having identical alleles (e.g., major or minor alleles of SNPs) at one or more genetic loci in homologous chromosome segments. "Homozygous" may also refer to a sample, a cell, a cell population, or a patient in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

Suitable polymorphism for the presently disclosed methods, kits, and arrays may include a polymorphism (or mutation) resulting in a Cys23Ser amino acid substitution, an rs3813929 (-759C/T) polymorphism, and an rs518147 (-697G/C) polymorphism). For example, the SNP referred to by dbSNP reference ID No. rs3813929 is located on the X chromosome, position 114584047, which may be a thymidine (T) in the minor allele or a cytosine (C) in the major allele; and the SNP referred to by dbSNP reference ID No. rs518147 is located on the X chromosome, position 114584109, which may be a cytosine (C) in the minor allele, or a guanine (G) in the major allele.

The present methods contemplate detecting a single nucleotide polymorphism (SNP). For example, the present methods may detect rs3813929 in either one or both alleles of the patient. (See rs3813929 SNP entry at the National Center for Biotechnology Information, which entry is incorporated herein by reference and refers to a C←→T transition at the reference nucleotide position, where the C-allele is the major allele and the T-allele is the minor allele). The present methods may detect a T-allele or a C-allele corresponding to the polymorphism (i.e., a T-nucleotide or a C-nucleotide at the position associated with the rs3813929). The present methods may detect whether a patient is homozygous or heterozygous for a T-allele or C-allele (i.e., whether the patient is TT, TC, or CC at the reference nucleotide position for rs3813929).

The present methods also may detect rs518147 in either one or both alleles of the patient. (See rs518147 SNP entry at the National Center for Biotechnology Information, which entry is incorporated herein by reference and refers to a G←→C transversion at the reference nucleotide position, where the G-allele is the major allele and the C-allele is the minor allele). The present methods may detect a G-allele or a C-allele corresponding to the polymorphism (i.e., a G-nucleotide or a C-nucleotide at the position associated with the rs518147). The present methods may detect whether a patient is homozygous or heterozygous for a G-allele or C-allele (i.e., whether the patient is GG, GC, or CC at the reference nucleotide position for rs518147).

The present methods may detect the polymorphism directly by analyzing chromosomal nucleic acid having the polymorphic variant sequence. Alternatively, the present method may detect the polymorphism indirectly by detecting an isoform nucleic acid expressed from the polymorphic variant sequence, by detecting an isoform polypeptide expressed from the polymorphic variant sequence, or by analyzing the expression of another nucleic acid or protein whose expression is regulated by the polymorphic sequence.

EXAMPLES

The following Example is illustrative and is not intended to limit the claimed subject matter.

Example—Association of Sertonin$_{2C}$ Receptor Polymorphisms with Antipsychotic Drug Response in Schizophrenia Abstract The serotonin (5-HT)$_{2C}$ receptor (HTR2C) has been implicated in schizophrenia and response to antipsychotic drugs (APDs) through its regulatory effect on dopamine release, interaction with scaffolding proteins at the synapse, and other unknown mechanisms. Evidence from genetic association studies also implicates HTR2C in a variety of neuropsychiatric diseases. We tested the association between HTR2C polymorphisms, Cys23Ser, -759C/T, and -697G/C, and treatment response in 171 schizophrenic patients after treatment with APDs, mostly clozapine, for 6 months.

We confirmed that -759C/T, but not Cys23Ser, was a cis-eQTL for HTR2C according to Braincloud data, an integrated database of genome-wide gene expression and genetic control in human postmortem dorsolateral prefrontal cortex (DLPFC) of normal subjects. Ser23 was significantly associated with treatment response at 6 months (positive symptoms, $X^2=7.540$, p=0.01; negative symptoms, $X^2=4.796$, p=0.03) in male, but not in female patients. Haplotype analysis showed that -759C-Ser23 maintained the same level of significant association with positive symptom improvement ($X^2=6.648$, p=0.01) but additive association with negative symptom improvement ($X^2=6.702$, p=0.01). Logistic regression after controlling for covariates showed these haplotypic associations remained significant with the same direction. Finally, a meta-analysis was performed on six studies with accessible genotyping data for rs6318 and treatment outcome. The overall odds ratio under fixed effect model is 2.00 (95% CI, 1.38-2.91, p=0.0003) and under random effect model is 1.94 (95% CI, 1.27-2.99, p=0.0024). In conclusion, HTR2C polymorphisms were associated with treatment response to clozapine in male schizophrenic patients. HTR2C could be relevant to a broad range of the psychopathology which responds to clozapine in schizophrenia.

Introduction

The $(5\text{-HT})_{2C}$ receptor (HTR2C), located at Xq24, belongs to a seven-transmembrane-spanning G protein-coupled receptor superfamily and mediates phospholipase C activation and subsequent excitation of a phosphatidylinositol-calcium second messenger system in neurons [1-3]. It is widely distributed in which are relevant to schizophrenia, such as the ventral tegmentum, nucleus accumbens, striatum, prefrontal cortex, and hippocampus.

1. HTR2C Associated with Schizophrenia and Treatment Response: Evidence from Neurobiology HTR2C receptors have a tonic inhibitory effect on dorsal and ventral striatal and cortical dopamine (DA) release [4,5], modulate serotonergic activity in the dorsal raphe[6], and suppress the increased serotonin and glutamate release in rat cortex following administration of the NMDA receptor antagonist 3-(R)-2-carboxypiperazin-4-propyl-1-phosphonic acid (CPP)[7].

HTR2C receptors also have potent interactions with a variety of scaffolding proteins, and play a key role in regulating synapse development and maintenance[8,9]. HTR2C interacts with several PDZ-domain-containing proteins. These proteins are actively involved in targeting and trafficking transmembrane proteins, such as PSD95 (DLG4), MPDZ, and a tripartite complex, Veli3-CASK-Mint1[9,10]. PSD95 forms multimeric scaffold complexes at postsynaptic sites, enabling clustering of receptors and associated signaling proteins, including the NMDA receptor, a key component of the hypoglutamatergic deficit postulated in schizophrenia[11] and an essential contributor to memory[12] In addition to its role in scaffolding macromolecular glutamatergic signaling complexes, PSD-95 profoundly modulates metabotropic HTR2A and HTR2C function. HTR2C is involved in the action of calcium/calmodulin-dependent serine protein kinases i.e. CASK, which is important for β-arrestin-dependent signaling[8]. Accumulated evidence suggests a role of β-arrestin-mediated pathway in schizophrenia and the mechanism of action of antipsychotic drugs (APDs) [8,13].

Some atypical APDs, e.g. clozapine, olanzapine, risperidone, and sertindole, are potent inverse agonists of both HTR2C and HTR2A receptors, whereas, quetiapine, and aripiprazole are not [14,15]. On the other hand, some typical APDs, e.g. chlorpromazine, thioridazine, spiperone, and thiothixene, are HTR2C neutral antagonists. HTR2C activation and inhibition of dopamine (DA) efflux in the cortex and limbic system indicate its involvement in cognition, psychosis, and addictive behaviors[1,3,16,17]. Blockade of the constitutive activity of HTR2C receptors has been implicated in enhancing cortical and limbic DA release by some APDs [17].

There is indirect evidence for enhanced mesolimbic DA release in response to an amphetamine challenge in drug-naïve schizophrenic patients. This has been interpreted as evidence that schizophrenic patients during an acute episode have increased presynaptic dopaminergic activity[18,19]. If so, the ability of HTR2C agonists to reduce DA release from terminals of VTA neurons in mesolimbic areas would be expected to have an antipsychotic effect. This has been demonstrated in vabicaserin[20]. In addition, reduced mRNA level of HTR2C has been reported in postmortem prefrontal cortex tissues of schizophrenia[21] and bipolar disorder[22]. Thus, there is extensive evidence that HTR2C is involved in the neurobiology of schizophrenia and the action of APDs.

2. HTR2C Associated with Schizophrenia and Treatment Response: Evidence from Genetic Association Studies Evidence from genetic association studies also implicates HTR2C in a variety of neuropsychiatric diseases. According to a comparative genome study on DNA methylation from great ape evolution to recent humans, the frequency of genetic variation is positively correlated with alterations in promoter methylation [23]. The HTR2C has a well-characterized promoter region harboring multiple polymorphisms, suggesting their potential impact on CpG methylation and putative transcription factor binding, resulting in alteration of HTR2C expression. rs3813929 (-759C/T) and rs518147 (-697G/C) are the most widely-investigated HTR2C promoter polymorphisms. -759C/T polymorphism is associated with antipsychotic induced weight gain [24]. -759C/T or -697G/C, has also been linked to therapeutic response to APDs[25,26]. However the results are contradictory with regard to gender and risk allele. rs6318, also known as Cys23Ser, is a non-synonymous SNP which results in an amino acid substitution of cysteine to serine at position 23. This substitution could disrupt a disulfide bridge and potentially alter the structure or stability of the HTR2C protein. This functional polymorphism has been found to be associated with neuropsychiatric diseases such as anorexia nervosa[27], unipolar and bipolar depression [28,29], and stress-related cortisol level [30]. It is unclear whether this SNP has any association with schizophrenia. A linkage study demonstrated no preferential transmission of either Cys or Ser alleles in 207 families with schizophrenia [31]. An association between the Cys23Ser and visual hallucinations and depression in schizophrenia patients is reported[32], but cannot be replicated by others[33,34]. Cys23Ser is also associated with chronic hospitalization [35], extrapyramidal side effects of APDs[36], psychotic symptoms in late-onset Alzheimer's disease[32], and migraine with aura [37]. rs6318 has also been linked to altered treatment response to clozapine[38,39]. How Cys23Ser impacts on HTR2C function is uncertain. The Ser23 variant has been associated with greater constitutive activity, lower affinity, and altered resensitization in some in vitro cell-line based functional assays [40,41] but not others[42,43]. Since clozapine has high affinity for HTR2C and acts as an inverse agonist[14], higher constitutive activity of Ser23 might mechanistically explain this association between rs6318 and treatment response to clozapine. The following studies on clozapine from other independent cohorts[44,45] [46] has failed to replicate this association.

Due to the inconsistent relationship between HTR2C polymorphism and psychopathology of schizophrenia and response to clozapine, the inconsistent results from functional activity assays, we examine all three widely-investigated HTR2C SNPs as possible predictors of response to treatment with APDs in schizophrenia in terms of positive and/or negative symptoms. Male and female are analyzed separately in order to determine whether the possible association has any gender preference. Finally a meta-analysis is performed to determine the overall association between HTR2C polymorphism and drug response (mainly clozapine).

Materials and Methods

Subjects

The 171 (male/female, 115/56) patients with schizophrenia or schizoaffective disorder who participated in this study were part of an NIMH-sponsored extramural clinical research center at Case Western Reserve University School of Medicine and Vanderbilt University School of Medicine. Details about recruitment and assessment of subjects have been reported previously [47]. Categorical treatment response was evaluated at 6 week and 6 months, using the criteria based upon Kane et al[48]. A reduction of >20% in Brief Psychiatric Rating Scale (BPRS) total or subscale scores was considered as responder. In cases where patients were very close to the operational criteria for response (>15% or <25%), a reduction of at least one category on the Clinical Global Impressions (CGI) scale was considered in order to enhance the definition of response. In the present study, patients were treated with standard doses of the following atypical antipsychotic drugs (clozapine, 78%; melperone, 7.0%; risperidone, 3.8%; or olanzapine, 2.1%) or typical antipsychotic drugs (9.0%). Antidepressants (14%) and mood stabilizers (5%) were used sparingly.

Genotyping

Blood samples for all the patients were processed with Qiagen genomic DNA extraction kit (Valencia, CA, USA) at the Center for Human Genetics Research Core at Vanderbilt University (Nashville, TN, USA). Taqman® assay for three SNPs, rs3813929 (-759C/T), rs518147(-697G/C), and rs6318 (Cys23Ser) in the HTR2C gene was performed on an ABI 7900HT Sequence Detection System (Applied Biosystems, Foster City, CA, USA). Genotype data for rs498207 from some samples was provided by the Clark Institute of Psychiatry (Toronto, Ontario, Canada). Call rates are 95.32%, 98.83%, and 97.66% for -759C/T, -670G/C, and Cys23Ser respectively.

Mapping Cis eQTL and Methylation QTL

BrainCloud allows the query of genome-wide gene expression data and their genetic control in human postmortem DLPFC of normal subjects across the lifespan[49]. We included all the SNP loci available within 200 kb interval (100 kb up- and downstream) of HTR2C transcript. The p value corresponds to the regression coefficient based on the residual expression level from the General Linear Model and the genotype obtained from 110 postnatal Caucasian subjects. We also inquire a genome-wide DNA methylation database, BrainCloud Methyl, derived from the same BrainCloud subjects [50], to see if those identified cis eQTLs have any impact on DNA methylation and considered as methylation QTLs.

Statistical Analysis

We analyzed the males and females separately because of functional uncertainty in heterozygous females due to either X chromosome inactivation (XCI) or other confounding factors related to gender difference, for example, a much stronger effect of the genetic association with clozapine-induced weight gain was observed in female subjects[51].

The relationship between genotypes and demographic variables was analyzed using chi-square ($\chi^2$) or ANOVA. P-values reported are two-tailed whenever applicable. Statistical significance was defined as $p<0.05$. As all results are considered exploratory, there was no adjustment for multiple comparisons. All individual SNP and haplotype association testing was conducted with PLINK 1.0.7[52]. Other statistical analysis was done by SPSS. Haplotype association analysis was performed for all possible combinations of SNPs (including consecutive and non-consecutive SNPs). For rs6318, genotypes were collapsed into a dominant model, separated by Ser carrier or non-carrier. Genotypes/haplotypes effects on the binary outcome were analyzed at 6 weeks, and 6 months by comparing the frequencies of alleles or genotypes between responder and non-responder groups using the following methods: Pearson's Chi-square, stepwise logistic regression controlled for multiple covariates including race, drug, age of onset, baseline score of BPRS subcategories, and status of early-responder. ANCOVA was also performed to test the association between HTR2C polymorphisms and percentage change (%) or absolute change (A) in BPRS total score and subcategories, after controlling for race and the corresponding baseline psychopathology. Linkage disequilibrium (LD) was visualized by Haploview. A SNP Annotation and Proxy Search (SNAP) was used to search proxy (tag) SNPs in LD with target SNPs from Hapmap database (release 21). Genotyping data from 1000Genome Database was extracted to confirm those tag SNPs are indeed in LD with target SNPs. Meta-analysis was performed by R 'meta' package under R Studio interface.

Results

Genotyping Quality Control and Demographic Data

Cys23Ser, -759C/T and -697G/C were genotyped for 171 Caucasian (118) and African-American (53) patients with schizophrenia. (See Table 1A (Male Patients) and Table 1B (Female Patients)). The relationship between genotypes and demographic variables was analyzed using chi-square ($\chi^2$) or ANOVA. P-values reported are two tailed whenever applicable. Statistical significance was defined as $p<0.05$.

TABLE 1A (Male Patients)

| Genotype | SNP ID | | | | | | | | |
|---|---|---|---|---|---|---|---|---|---|
| | rs3813929 | | | rs518147 | | | rs6318 | | |
| | T/T | C/C | P value | C/C | G/G | P value | Ser carrier | Ser non-carrier | P value |
| Counts | 17 | 100 | | 40 | 77 | | 24 | 90 | |
| Frequency | 0.14 | 0.86 | | 0.34 | 0.66 | | 0.22 | 0.78 | |
| Total BPRS | 27.88 ± 17.51 | 30.57 ± 12.08 | 0.43 | 32.3 ± 14.9 | 29.08 ± 11.78 | 0.2 | 34.92 ± 12.30 | 29.03 ± 12.89 | 0.04 |
| Positive 4 items | 9.41 ± 7.20 | 11.22 ± 5.36 | 0.23 | 11.4 ± 5.74 | 10.73 ± 5.65 | 0.54 | 12.69 ± 4.14 | 10.59 ± 5.81 | 0.09 |
| Positive 3 items | 7.47 ± 5.91 | 9.04 ± 4.72 | 0.23 | 9.282 ± 4.91 | 8.55 ± 4.94 | 0.45 | 10.25 ± 3.53 | 8.57 ± 5.04 | 0.13 |
| Negative 3 items | 3.94 ± 2.33 | 4.43 ± 3.01 | 0.53 | 4.15 ± 2.94 | 4.47 ± 2.91 | 0.58 | 4.65 ± 3.03 | 4.30 ± 2.87 | 0.59 |
| Anxiety/Depression | 4.69 ± 2.87 | 4.99 ± 3.67 | 0.75 | 5.39 ± 3.49 | 4.72 ± 3.59 | 0.35 | 5.24 ± 3.70 | 5.00 ± 3.48 | 0.72 |
| Age onset (year) | 20 ± 6.24 | 20.26 ± 5.12 | 0.86 | 20.75 ± 6.36 | 19.93 ± 4.60 | 0.43 | 22.78 ± 7.83 | 19.57 ± 4.27 | 0.01 |
| Duration of illness (year) | 11.71 ± 11.34 | 12.21 ± 7.45 | 0.81 | 11.63 ± 9.50 | 12.41 ± 7.26 | 0.62 | 10.61 ± 8.63 | 12.42 ± 8.01 | 0.34 |
| No. of hospitalization | 4.38 ± 4.24 | 6.66 ± 7.15 | 0.22 | 4.54 ± 4.09 | 7.28 ± 7.78 | 0.05 | 4.76 ± 4.13 | 6.56 ± 6.96 | 0.26 |
| Treatment resistant (%) | 52.9 | 70.0 | 0.17 | 60 | 71.4 | 0.21 | 62.5 | 68.9 | 0.55 |
| Baseline Unmedicated (%) | 81.3 | 76.9 | | 78.4 | 77.1 | 0.88 | 72.7 | 78.0 | 0.6 |
| Clozapine treated (%) | 82.4 | 74.0 | 78.7 | 85.0 | 72.7 | 0.34 | 83.3 | 74.4 | 0.28 |
| Ethnicity[1] | | | 0.004 | | | 0.19 | | | 0.04 |
| Caucasian | 12 | 67 | | 24 | 55 | | 11 | 66 | |
| Afro-American | 5 | 33 | | 16 | 22 | | 13 | 24 | |

[1]Self-described ethnicity.

TABLE 1B (Female Patients)

| Genotype | SNP ID | | | | | |
|---|---|---|---|---|---|---|
| | rs3813929 | | | rs518147 | | |
| | T/T | C/C | P value | C/C | C/G | |
| Counts | 3 | 41 | | 7 | 24 | |
| Frequency | 0.07 | 0.93 | | 0.13 | 0.46 | |
| Total BPRS | 28.33 ± 9.29 | 34.27 ± 11.48 | 0.39 | 30.86 ± 11.85 | 35.71 ± 11.75 | |
| Positive 4 items | 8.33 ± 6.11 | 12.66 ± 4.52 | 0.12 | 11.14 ± 6.67 | 13.58 ± 4.39 | |
| Positive 3 items | 7 ± 5.29 | 11.03 ± 3.93 | 0.1 | 10 ± 6.83 | 11.78 ± 3.57 | |
| Negative 3 items | 3.33 ± 3.22 | 4.39 ± 3.31 | 0.6 | 4 ± 3.74 | 4.5 ± 2.70 | |
| Anxiety/Depression | 7.33 ± 4.73 | 6.42 ± 4.12 | 0.71 | 6.14 ± 3.53 | 5.75 ± 3.92 | |
| Age onset (year) | 20.33 ± 4.04 | 21.55 ± 5.85 | 0.73 | 21 ± 4.08 | 21.30 ± 5.47 | |
| Duration of illness (year) | 14 ± 15.59 | 11.63 ± 7.27 | 0.62 | 15.29 ± 11.41 | 14.74 ± 7.81 | |
| No. of hospitalization | 3 ± 2.83 | 8.11 ± 8.74 | 0.42 | 4.5 ± 3.14 | 7 ± 5.51 | |
| Treatment resistant (%) | 66.7 | 70.7 | 0.88 | 71.4 | 79.2 | |
| Baseline Unmedicated (%) | 100.0 | 63.6 | 0.29 | 66.7 | 78.9 | |
| Clozapine treated (%) | 66.7 | 85.4 | 0.1 | 71.4 | 87.5 | |
| Ethnicity[1] | | | 0.2 | | | |
| Caucasian | 3 | 26 | | 6 | 16 | |
| Afro-American | 0 | 15 | | 1 | 8 | |

| Genotype | SNP ID | | | | |
|---|---|---|---|---|---|
| | rs518147 | | rs6318 | | |
| | G/G | P value | Ser carrier | Ser non-carrier | P value |
| Counts | 21 | | 20 | 33 | |
| Frequency | 0.4 | | 0.38 | 0.62 | |
| Total BPRS | 33.81 ± 10.61 | 0.8 | 34.9 ± 14.41 | 33.82 ± 8.40 | 0.73 |
| Positive 4 items | 12 ± 4.89 | 0.91 | 12.9 ± 5.18 | 12.15 ± 4.76 | 0.58 |

TABLE 1B-continued (Female Patients)

|  |  |  |  |  |  |
|---|---|---|---|---|---|
| Positive 3 items | 10.43 ± 4.06 | 0.83 | 11.2 ± 4.95 | 10.5 ± 4.2 | 0.58 |
| Negative 3 items | 4.76 ± 3.90 | 0.61 | 4.43 ± 3.01 | 4.62 ± 3.46 | 0.84 |
| Anxiety/Depression | 6.91 ± 4.44 | 0.48 | 6.05 ± 3.94 | 6.27 ± 4.03 | 0.85 |
| Age onset (year) | 21.29 ± 5.68 | 0.99 | 21.79 ± 4.85 | 21.58 ± 6.27 | 0.9 |
| Duration of illness (year) | 10 ± 6.51 | 0.1 | 13.05 ± 6.96 | 12.49 ± 8.73 | 0.81 |
| No. of hospitalization | 9.4 ± 10.21 | 0.35 | 7.94 ± 9.50 | 7.03 ± 6.79 | 0.71 |
| Treatment resistant (%) | 61.9 | 0.44 | 80 | 69.7 | 0.41 |
| Baseline Unmedicated (%) | 61.1 | 0.49 | 60.0 | 72.4 | 0.4 |
| Clozapine treated (%) | 90.5 | 0.003 | 90.9 | 75.0 | 0.14 |
| Ethnicity[1] |  | 0.62 |  |  | 0.08 |
| Caucasian | 15 |  | 12 | 27 |  |
| Afro-American | 6 |  | 8 | 6 |  |

[1]Self-described ethnicity.

Hardy-Weinberg equilibrium (HWE) test for female Caucasian subjects was not significant (p<0.01), except for rs3813929 (p=0.003), due to a lack of patients with the heterozygous genotype. We further genotyped 300 more schizophrenic subjects and HWE test wasn't significant (p=0.45), suggesting this departure from HWE is related to small sample size (n=53) and low minor allele frequency (MAF) for rs3813929 (14.93% in 1000Genome data; 10.35% in our samples) in the female Caucasians. (See Table 2).

Figure 3:
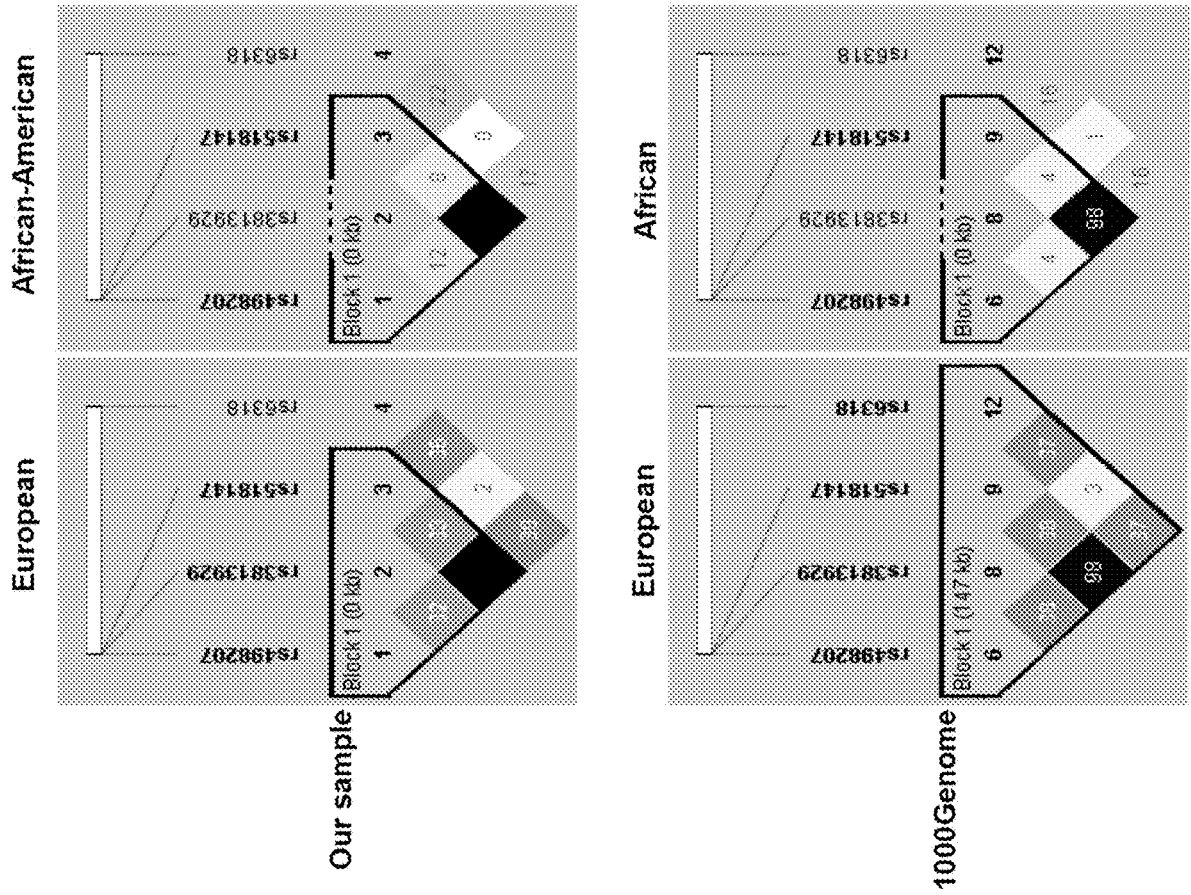
FIG. 3. Haploview plot of HTR2C SNPs in the tested sample and 1000 genome sample stratified by ethnicity (European or African-American).

Although the D' was equal to one (data not show), the $r^2$ was very low. (See FIG. 3), suggesting gene conversion happened. We indeed, observed a recombination event, >40 cM/Mb recombination rate, in the boundary between promoter and transcriptional starting, based on regional LD plot generated from SNAP (data not shown).

In the male group, the age at onset for the Ser23 carriers was significantly older than that for non-carriers (p=0.009). (See Table 1A). This difference was not observed in the female group (p=0.899). (See Table 1B). There was no

TABLE 2

Summary of genotypic distribution of three mostly investigated HTR2C SNPs in Caucasians from 1000Genome, Braincloud, and our data.

| rs3813929 | Female | | | Male | | |
|---|---|---|---|---|---|---|
| Datasource | TT | TC | CC | T | C | tag SNP |
| 1000 genome | 2 (1%) | 56 (27.9%) | 143 (71.1%) | 32 (18%) | 146 (82%) | rs3813929 |
| Braincloud | 1 (3.1%) | 5 (15.6%) | 26 (81.3%) | 17 (21.8%) | 61 (78.2%) | rs 12846241 |
| Our sample | 3 (10.3%) | 0 (0%) | 26 (89.7%) | 12 (15.2%) | 67 (84.8%) | rs3813929 |

| rs518147 | Female | | | Male | | |
|---|---|---|---|---|---|---|
| Datasource | CC | CG | GG | C | G | tag SNP |
| 1000 genome | 16 (8%) | 92 (45.8%) | 93 (46.3%) | 67 (37.6%) | 111 (62.4%) | rs498207 |
| 1000 genome | 17 (8.4%) | 91 (45.3%) | 93 (46.3%) | 66 (37.1%) | 112 (62.9%) | rs518147 |
| Braincloud | 3 (9.4%) | 12 (37.5%) | 17 (53.1%) | 39 (50%) | 39 (50%) | rs498207 |
| Our sample | 3 (12%) | 8 (32%) | 14 (56%) | 23 (33.8%) | 45 (66.2%) | rs498207 |
| Our sample | 6 (16.2%) | 16 (43.2%) | 15 (40.6%) | 24 (30.4%) | 55 (69.6%) | rs518147 |

| rs6318 | Female | | | Male | | |
|---|---|---|---|---|---|---|
| Datasource | CC | CG | GG | C | G | tag SNP |
| 1000 genome | 4 (2%) | 51 (25.4%) | 146 (72.6%) | 32 (18%) | 146 (82%) | rs6318 |
| Braincloud | 2 (6.7%) | 4 (13.3%) | 24 (80%) | 19 (24.4%) | 59 (75.6%) | rs5987834 |
| Our sample | 2 (4.8%) | 12 (28.5%) | 28 (66.7%) | 14 (16.7%) | 70 (83.3%) | rs6318 |

Three datasets were genotyped by illumina next-generation sequencing, illumina Beadarray, and ABI Taqman assay, respectively.
Data was presented as genotype count (% in Female or Male subjects).

The haplotype view was generated for our sample and 1000Genome sample separated by ethnicity. (See FIG. 3). The LD patterns ($r^2$) are comparable and consistent between the two samples, suggesting our genotype data are reliable and representative. Interestingly, the genotype frequency between rs3813929 and rs6318 are very similar across three Caucasian datasets (1000Genome, Braincloud, and ours) according to Table 2.

significant difference in the proportions of patients who were treatment resistant or unmedicated at baseline between the genotypes for each SNP. Duration of illness and number of previous hospitalization also did not differ. Although Ser carriers had a higher total BRPS score in the male patients (borderline significance, p=0.04), there was no significant difference with regard to the subcategories of psychopathology including positive, negative, and anxiety/depression subscales. Race, drug, age of onset were included as covariates in the following regression analysis.

Rs3813929 is cis-eQTL for HTR2C

We successfully identified the tag SNP, which are in LD with the candidate SNPs ($r^2>0.85$) by SNAP, based on earlier Hapmap data (21) in Caucasians. We confirmed those tag SNP are indeed, in LD with three candidates by a haploview analysis of the acquired genotype data from 1000Genome. (See FIG. 1). rs12846241 ($r^2=0.96$), rs498207 ($r^2=0.98$) and rs5987834 ($r^2=0.86$) are the tag SNPs, genotyped in Braincloud, for rs3813929, rs518147 and rs6318, respectively, in Caucasians. A single expression probe selected for HTR2C is located in the 3' end of mRNA. (See FIG. 1, which represents the major form of HTR2C cloned from multiple brain regions according to NCBI Aceview). For the cis association analysis, we initially identified six SNPs associated with gene expression (p<0.05). (See FIG. 1). Examining postnatal subjects separated by gender, this association becomes stronger in males, but not in females and more cis eQTLs were identified. (See Table 3).

polymorphism and % methylation in this CpG site, in BrainCloud Methyl. We confirmed this significant association between rs3813929 genotype and DNA methylation (p=0.0005 for rs11798015 or 0.009 for rs12846241). Whereas for rs518147, this association has a borderline significance (p=0.096 by rs498207 or 0.021 by rs547617). rs6318, tagged by rs5987834, has no impact on gene expression and % methylation. In rs3813929, T but not C, allele was associated with lower expression and higher methylation rate. We emphasize this association between rs3817929 and DNA methylation because the epigenetic markers may not be reproduced in in vitro gene-reporter system which is commonly used to confirm the functional activity of a putative genetic variant in a promoter region. The same trend of association, though not always significant due to limited number of subjects, was observed in Braincloud African-American sample (see Table 3), suggesting that rs3813929 is a functional variant for HTR2C independent of ethnicity. It is noted that all the above findings do not apply for Braincloud females.

TABLE 3

A list of potential cis-eQTLs and methylation-QTLs identified by Braincloud and Brainmethyl database.

| SNP ID | Minor Allele | Observed Genotype | Location | SNP in promoter | MAF (M/F) | Tag SNP | Cis-eQTL (AA/EUR) | Methylation-QTL (AA/EUR) |
|---|---|---|---|---|---|---|---|---|
| rs489736 | A | A/G | Intergenic-5' | No | 0.382/0.316 | | 0.058/0.045 | 0.002/0.002 |
| rs11798015 | G | G/A | Intergenic-5' | No | 0.152/0.154 | rs3813929 (LD) | NA/0.004 | NA/0.000 |
| rs547617 | G | G/A | Intergenic-5' | No | 0.371/0.313 | rs518147 (LD) | 0.162/0.043 | 0.003/0.021 |
| rs3795182 | G | G/A | near-gene-5' | Yes | 0.185/0.149 | | NA | NA |
| rs521018 | G | G/T | near-gene-5' | Yes | 0.376/0.309 | | NA | NA |
| rs498207 | G | G/A | near-gene-5' | Yes | 0.376/0.309 | rs518147 (LD) | 0.267/0.043 | 0.014/0.096 |
| rs3813928 | A | A/G | near-gene-5' | Yes | 0.180/0.149 | rs3813929 (LD) | NA | NA |
| rs3813929 | T | T/C | near-gene-5' | Yes | 0.180/0.149 | −759 (C/T) | NA | NA |
| rs518147 | C | C/G | untranslated-5' | Yes | 0.371/0.311 | −697 (G/C) | NA | NA |
| rs12846241 | G | G/T | intron | No | 0.180/0.152 | rs3813929 (LD) | 0.116/0.006 | 0.205/0.009 |
| rs12690355 | G | G/A | intron | No | 0.191/0.154 | rs3813929 (LD) | NA/0.016 | NA/0.028 |
| rs6318 | C | C/G | exon | No | 0.180/0.147 | cys23ser | NA | NA |
| rs4911871 | G | G/A | intron | No | 0.202/0.179 | | NA/0.009 | NA/0.002 |
| rs6644093 | T | T/G | intron | No | 0.146/0.132 | | NA/0.004 | NA/0.007 |
| rs5987834 | T | T/C | Intergenic-3' | No | 0.185/0.142 | rs6318 (LD) | 0.914/0.601 | 0.561/0.944 |

MAF = minor allele frequency.
M = male; F = female.
AA = African American; Eur = European.
NA represents data not available or not reported due to low MAF resulting in unreliable data, $r^2 > 0.85$ in LD.
SNPs are located in promoter region and putative CpG Island. Rs6318 and its tag SNP, rs5987834, exclusively available in Braincloud were negative controls.
p < 0.01 is cut-off value for cis-eQTLs.
0.01 > P < 0.05 suggest a possible impact of that SNP on gene expression.

This discrepancy could be a result of low MAF in the Braincloud female sample, XCI, or other confounding factors related to gender difference. All the identified cis eQTLs are listed in Table 3. Most of them are aggregated at the promoter or 5'UTR regions as expected. (See FIG. 1). rs3813929, tagged by rs12846241, has been confirmed as cis-eQTL for HTR2C. The T genotype has a lower mRNA level than C genotype (p=0.006), which is in conflict to some reported in vitro gene-reporter assays[53,54]. rs518147, tagged by rs498207, also suggests potential impact on gene expression (p=0.043), but not as strong as rs3813929. This finding echoed the earlier EMSA finding [55] that rs3813929, but not rs518147, altered DNA-protein interactions, leading to change in expression of HTR2C. Haplotype analysis of rs3813929-rs518147, tagged by rs12846241-rs498207, showed that male Caucasians with C-G (n=39) and C-C (n=22) genotypes had a significantly higher expression of HTR2C than those with T-C (n=17) genotype (corresponding p=0.007 and p=0.050). Since rs3813929 and rs518147 are located in a putative CpG island. (See FIG. 1), we also evaluated the relationship between the genetic Genotype/Haplotype Association Study Based on the previous studies (genetic and functional) and our cis eQTL findings, rs3813929, rs6318, rs518147, and the combinations of two or all three, were targets for the subsequent genotype-phenotype association study. Since in vitro functional assays indicated that rs3813929 and rs6318 have a significant impact on HTR2C activity through distinct mechanisms, we further explored if -759C-Ser, "a super combination", as we proposed to produce a greater expression of the constitutively more active form of HTR2C, may demonstrate an even stronger association with dichotomous symptom improvement in an additive mode, after treatment with the HTR2C inverse agonists or antagonists studied here.

A significant association between rs6318 and dichotomous treatment response was observed only in the male group for both positive symptoms, $X^2=7.540$, p=0.006; and negative symptoms, $X^2=4.796$, p=0.029. (See Table 4).

TABLE 4

Haplotype association analysis of HTR2C SNPs with treatment response by Chi-square test in male patients.

| | | | BPRS Positive 4 Items | | BPRS Positive 3 Items | |
|---|---|---|---|---|---|---|
| Male Only SNP ID | Haplotype | Haplotype frequency | Frequency in Responder/non-responder | $X^2/P$ | Frequency in Responder/non-responder | $X^2/P$ |
| rs3813929 (−759) | C | 0.861 | 0.810/0.877 | 0.861/0.353 | 0.851/0.851 | 0/1 |
| rs518147 (−697) | C | 0.336 | 0.452/0.263 | 3.84/0.050 | 0.447/0.255 | 3.782/0.052 |
| rs6318 (Cys23Ser) | Ser carrier | 0.22 | 0.289/0.161 | 2.406/0.121 | 0.34/0.106 | 7.54/0.006 |
| rs3813929-rs518147 | C-C | 0.197 | 0.262/0.140 | 2.304/0.129 | 0.298/0.106 | 5.343/0.021 |
| rs518147-rs6318 | C-Ser | 0.176 | 0.244/0.125 | 2.315/0.128 | 0.283/0.085 | 6.07/0.014 |
| rs3813929-rs6318 | C-Ser | 0.202 | 0.268/0.161 | 1.674/0.196 | 0.326/0.106 | 6.648/0.010 |
| rs3813929-rs518147-rs6318 | C-C-Ser | 0.171 | 0.238/0.123 | 2.26/0.133 | 0.277/0.085 | 5.817/0.016 |

| | | BPRS Negative 3 Items | | Anxiety/Depression 3 Items | |
|---|---|---|---|---|---|
| Male Only SNP ID | | Frequency in Responder/non-responder | $X^2/P$ | Frequency in Responder/non-responder | $X^2/P$ |
| rs3813929 (−759) | | 0.838/0.818 | 0.059/0.807 | 0.84/0.848 | 0.011/0.916 |
| rs518147 (−697) | | 0.405/0.291 | 1.298/0.255 | 0.34/0.348 | 0.007/0.936 |
| rs6318 (Cys23Ser) | | 0.308/0.125 | 4.796/0.029 | 0.25/0.196 | 0.414/0.520 |
| rs3813929-rs518147 | | 0.243/0.109 | 2.917/0.088 | 0.18/0.196 | 0.039/0.844 |
| rs518147-rs6318 | | 0.243/0.093 | 3.828/0.050 | 0.184/0.178 | 0.006/0.941 |
| rs3813929-rs6318 | | 0.306/0.093 | 6.702/0.010 | 0.225/0.2 | 0.084/0.772 |
| rs3813929-rs518147-rs6318 | | 0.222/0.091 | 3.064/0.080 | 0.18/0.174 | 0.006/0.938 |

Positive 4-item includes suspiciousness, hallucinatory behavior, unusual thought content, and conceptual disorganization.
Positive 3-item = Positive 4-item without "concept disorganization".
Male and female subjects were analyzed separately.

Haplotype analysis showed that -759C-Ser maintained the same level of significant association with positive symptom improvement ($X^2=6.648$, p=0.010) and additive association with negative symptom improvement ($X^2=6.702$, p=0.010) when comparing to the association between Ser alone and dichotomous variables. (See Table 4). Logistic regression after controlling for race, age of onset, and drugs showed the haplotype results remained similar significance in the male group. None of the covariates had a significant impact on this association (p>0.05). Since baseline BPRS level may be a strong predictor of treatment response, we included it as a covariate. Ser alone still showed the most significant association with positive symptom improvement across all the haplotype combinations (OR=3.63; p=0.030). (See Table 5).

TABLE 5

Haplotype association of HTR2C SNPs with treatment response analyzed by logistic regression. Data were presented as Odds Ratio/P value.

| | | | BPRS Positive 3 Items | | BPRS Negative 3 Items | |
|---|---|---|---|---|---|---|
| Male Only SNPID | Haplotype | Haplotype Frequency | Add Covar (Early response status) | Add Covar (Baseline BPRS) | Add Covar (Early response status) | Add Covar (Baseline BPRS) |
| rs3813929 (−759) | C | 0.861 | 1.25/0.724 | 1.02/0.979 | 1.81/0.413 | 1.09/0.891 |
| rs518147(−697) | C | 0.336 | 1.85/0.205 | 2.05/0.134 | 1.63/0.371 | 1.75/0.25 |
| rs6318 (Cys23Ser) | Ser carrier | 0.22 | 3.7/0.034 | 3.63/0.030 | 3.69/0.048 | 2.99/0.057 |
| rs3813929-rs518147 | C-C | 0.197 | 3.05/0.074 | 2.83/0.081 | 3.83/0.054 | 2.69/0.113 |
| rs518147-rs6318 | C-Ser | 0.176 | 3.51/0.057 | 3.33/0.061 | 4.6/0.036 | 3.19/0.075 |
| rs3813929-rs6318 | C-Ser | 0.202 | 3.6/0.040 | 3.4/0.042 | 4.89/0.025 | 3.94/0.030 |
| rs3813929-rs518147-rs6318 | C-C-Ser | 0.171 | 3.44/0.062 | 3.21/0.067 | 4.52/0.040 | 2.97/0.100 |
| No. of subjects (EUR/AA) | | | 72/35 | 69/24 | 74/33 | 71/26 |

Positive 3-item includes suspiciousness, hallucinatory behavior, and unusual thought content.
Male and female subjects were analyzed separately.
5A-B, Data was adjusted for Race and Drug.
5C-D, Data was adjusted for baseline score for psychopathology or status of early responder at 6-week assessment.

TABLE 3

A list of potential cis-eQTLs and methylation-QTLs identified by Braincloud and Brainmethyl database.

| SNP ID | Minor Allele | Observed Genotype | Location | SNP in promoter | MAF (M/F) | Tag SNP | Cis-eQTL (AA/EUR) | Methylation-QTL (AA/EUR) |
|---|---|---|---|---|---|---|---|---|
| rs489736 | A | A/G | Intergenic-5' | No | 0.382/0.316 |  | 0.058/0.045 | 0.002/0.002 |
| rs11798015 | G | G/A | Intergenic-5' | No | 0.152/0.154 | rs3813929 (LD) | NA/0.004 | NA/0.000 |
| rs547617 | G | G/A | Intergenic-5' | No | 0.371/0.313 | rs518147 (LD) | 0.162/0.043 | 0.003/0.021 |
| rs3795182 | G | G/A | near-gene-5' | Yes | 0.185/0.149 |  | NA | NA |
| rs521018 | G | G/T | near-gene-5' | Yes | 0.376/0.309 |  | NA | NA |
| rs498207 | G | G/A | near-gene-5' | Yes | 0.376/0.309 | rs518147 (LD) | 0.267/0.043 | 0.014/0.096 |
| rs3813928 | A | A/G | near-gene-5' | Yes | 0.180/0.149 | rs3813929 (LD) | NA | NA |
| rs3813929 | T | T/C | near-gene-5' | Yes | 0.180/0.149 | −759 (C/T) | NA | NA |
| rs518147 | c | C/G | untranslated-5' | Yes | 0.371/0.311 | −697 (G/C) | NA | NA |
| rs12846241 | G | G/T | intron | No | 0.180/0.152 | rs3813929 (LD) | 0.116/0.006 | 0.205/0.009 |
| rs12690355 | G | G/A | intron | No | 0.191/0.154 | rs3813929 (LD) | NA/0.016 | NA/0.028 |
| rs6318 | C | C/G | exon | No | 0.180/0.147 | cys23ser | NA | NA |
| rs4911871 | G | G/A | intron | No | 0.202/0.179 |  | NA/0.009 | NA/0.002 |
| rs6644093 | T | T/G | intron | No | 0.146/0.132 |  | NA/0.004 | NA/0.007 |
| rs5987834 | T | T/C | Intergenic-3' | No | 0.185/0.142 | rs6318 (LD) | 0.914/0.601 | 0.561/0.944 |

MAF = minor allele frequency.

M = male; F = female.

AA = African American; Eur = European.

NA represents data not available or not reported due to low MAF resulting in unreliable data, $r^2 > 0.85$ in LD.

SNPs are located in promoter region and putative CpG Island. Rs6318 and its tag SNP, rs5987834, exclusively available in Braincloud were negative controls.

p < 0.01 is cut-off value for cis-eQTLs.

$0.01 > P < 0.05$ suggest a possible impact of that SNP on gene expression.

TABLE 4

Haplotype association analysis of HTR2C SNPs with treatment response by Chi-square test in male patients.

| Male Only SNP ID | Haplotype | Haplotype frequency | BPRS Positive 4 Items Frequency in Responder/non-responder | $X^2$/P | BPRS Positive 3 Items Frequency in Responder/non-responder | $X^2$/P |
|---|---|---|---|---|---|---|
| rs3813929 (−759) | C | 0.861 | 0.810/0.877 | 0.861/0.353 | 0.851/0.851 | 0/1 |
| rs518147 (−697) | C | 0.336 | 0.452/0.263 | 3.84/0.050 | 0.447/0.255 | 3.782/0.052 |
| rs6318 (Cys23Ser) | Ser carrier | 0.22 | 0.289/0.161 | 2.406/0.121 | 0.34/0.106 | 7.54/0.006 |
| rs3813929-rs518147 | C-C | 0.197 | 0.262/0.140 | 2.304/0.129 | 0.298/0.106 | 5.343/0.021 |
| rs518147-rs6318 | C-Ser | 0.176 | 0.244/0.125 | 2.315/0.128 | 0.283/0.085 | 6.07/0.014 |
| rs3813929-rs6318 | C-Ser | 0.202 | 0.268/0.161 | 1.674/0.196 | 0.326/0.106 | 6.648/0.010 |
| rs3813929-rs518147-rs6318 | C-C-Ser | 0.171 | 0.238/0.123 | 2.26/0.133 | 0.277/0.085 | 5.817/0.016 |

| Male Only SNP ID | BPRS Negative 3 Items Frequency in Responder/non-responder | $X^2$/P | Anxiety/Depression 3 Items Frequency in Responder/non-responder | $X^2$/P |
|---|---|---|---|---|
| rs3813929 (−759) | 0.838/0.818 | 0.059/0.807 | 0.84/0.848 | 0.011/0.916 |
| rs518147 (−697) | 0.405/0.291 | 1.298/0.255 | 0.34/0.348 | 0.007/0.936 |
| rs6318 (Cys23Ser) | 0.308/0.125 | 4.796/0.029 | 0.25/0.196 | 0.414/0.520 |
| rs3813929-rs518147 | 0.243/0.109 | 2.917/0.088 | 0.18/0.196 | 0.039/0.844 |
| rs518147-rs6318 | 0.243/0.093 | 3.828/0.050 | 0.184/0.178 | 0.006/0.941 |
| rs3813929-rs6318 | 0.306/0.093 | 6.702/0.010 | 0.225/0.2 | 0.084/0.772 |
| rs3813929-rs518147-rs6318 | 0.222/0.091 | 3.064/0.080 | 0.18/0.174 | 0.006/0.938 |

Positive 4-item includes suspiciousness, hallucinatory behavior, unusual thought content, and conceptual disorganization.

Positive 3-item = Positive 4-item without "concept disorganization".

Male and female subjects were analyzed separately.

TABLE 5

Haplotype association of HTR2C SNPs with treatment response analyzed by logistic regression. Data were presented as Odds Ratio/P value.

| Male Only SNP ID | Haplotype | Haplotype Frequency | BPRS Positive 3 Items | | BPRS Negative 3 Items | |
|---|---|---|---|---|---|---|
| | | | Add Covar (Early response status) | Add Covar (Baseline BPRS) | Add Covar (Early response status) | Add Covar (Baseline BPRS) |
| rs3813929 (−759) | C | 0.861 | 1.25/0.724 | 1.02/0.979 | 1.81/0.413 | 1.09/0.891 |
| rs518147(−697) | C | 0.336 | 1.85/0.205 | 2.05/0.134 | 1.63/0.371 | 1.75/0.25 |
| rs6318 (Cys23Ser) | Ser carrier | 0.22 | 3.7/0.034 | 3.63/0.030 | 3.69/0.048 | 2.99/0.057 |
| rs3813929-rs518147 | C-C | 0.197 | 3.05/0.074 | 2.83/0.081 | 3.83/0.054 | 2.69/0.113 |
| rs518147-rs6318 | C-Ser | 0.176 | 3.51/0.057 | 3.33/0.061 | 4.6/0.036 | 3.19/0.075 |
| rs3813929-rs6318 | C-Ser | 0.202 | 3.6/0.040 | 3.4/0.042 | 4.89/0.025 | 3.94/0.030 |
| rs3813929-rs518147-rs6318 | C-C-Ser | 0.171 | 3.44/0.062 | 3.21/0.067 | 4.52/0.040 | 2.97/0.100 |
| No. of subjects (EUR/AA) | | | 72/35 | 69/24 | 74/33 | 71/26 |

Positive 3-item includes suspiciousness, hallucinatory behavior, and unusual thought content.
Male and female subjects were analyzed separately.
5A-B, Data was adjusted for Race and Drug.
5C-D, Data was adjusted for baseline score for psychopathology or status of early responder at 6-week assessment.

−759C-Ser showed the strongest relationship to negative symptom improvement (OR=3.94; p=0.030). The low MAF (0.09) of -759C/T in African-Americans and relatively lower call rates (95.32%), as compared to other SNPs (98.83% and 97.66%) in our study, may account for not observing the additive association between -759C-Ser and positive symptom improvement. rs518147 had no add-on effect on this association when comparing rs3813929-rs518147-rs6318 with rs3813929-rs6318 or comparing rs6318-rs518147 with rs6318 alone. However, rs3813929-rs518147 demonstrated a trend of association with dichotomous variables (corresponding OR=2.83, p=0.081 or OR=2.69, p=0.1 for positive or negative symptoms) despite rs518147 or rs3813929 alone showing no significant association at all. (See Table 5), suggesting that rs518147 does have a minor functional impact on HTR2C biology. This positive finding with dichotomous positive 3-item improvement is not found when using dichotomous positive 4-item improvement which includes conceptual disorganization. 11% of patients were not available for the 6-month clinical assessment. The majority of the drop-outs were African-Americans (78.9%). The drop-outs may potentially underestimate the true association between the genetic variants and treatment response. Although this drop-out may be unrelated to response status at 6-week assessment (50% drop-offs are early responders), we still considered it as a covariate in our study. Once again, Logistic regression after adding this covariate showed a similar result with the same trend. (See Table 5). This pattern of haplotype association was not observed in the 6-week assessment. All of the above significant findings were only observed in the male patients except for a borderline significance for rs6318 associated with negative symptom improvement in female ($X^2$=3.9, p=0.048). (See Table 6).

TABLE 6

Haplotype association analysis of HTR2C SNPs with treatment response by Chi-square test in female patients and all patients.

| Female Only SNP ID | Haplotype | Haplotype frequency | BPRS Positive 4 Items | | BPRS Positive 3 Items | | BPRS Negative 3 Items | |
|---|---|---|---|---|---|---|---|---|
| | | | Frequency in Responder/non-responder | $X^2$/P | Frequency in Responder/non-responder | $X^2$/P | Frequency in Responder/non-responder | $X^2$/P |
| rs3813929 (−759) | C | 0.936 | 0.95/0.846 | 2.056/0.152 | 0.95/0.833 | 2.403/0.121 | 0.833/0.941 | 1.764/0.184 |
| rs518147 (−697) | C | 0.364 | 0.333/0.438 | 0.889/0.346 | 0.326/0.438 | 1.003/0.317 | 0.385/0.370 | 0.0161/0.899 |
| rs6318 (Cys23Ser) | Ser carrier | 0.397 | 0.296/0.438 | 1.764/0.184 | 0.32/0.375 | 0.263/0.608 | 0.4667/0.25 | 3.9/0.048 |
| rs3813929-rs518147 | C-C | 0.25 | 0.211/0.231 | 0.037/0.847 | 0.211/0.208 | 0.000/0.984 | 0.136/0.235 | 0.828/0.363 |
| rs518147-rs6318 | C-Ser | 0.213 | 0.188/0.219 | 0.117/0.732 | 0.196/0.188 | 0.008/1 | 0.192/0.174 | 0.038/0.846 |
| rs3813929-rs6318 | C-Ser | 0.413 | 0.3/0.462 | 1.777/0.183 | 0.3/0.417 | 0.905/0.341 | 0.417/0.294 | 0.935/0.333 |
| rs3813929-rs518147-rs6318 | C-C-Ser | 0.205 | 0.18/0.219 | 0.187/0.666 | 0.188/0.188 | 0/1 | 0.179/0.174 | 0.003/0.959 |

| Male + Female SNP ID | Haplotype | Haplotype frequency | BPRS Positive 4 Items | | BPRS Positive 3 Items | | BPRS Negative 3 Items | |
|---|---|---|---|---|---|---|---|---|
| | | | Frequency in Responder/non-responder | $X^2$/P | Frequency in Responder/non-responder | $X^2$/P | Frequency in Responder/non-responder | $X^2$/P |
| rs3813929 (−759) | C | 0.894 | 0.878/0.868 | 0.0416/0.839 | 0.897/0.845 | 0.937/0.333 | 0.836/0.865 | 0.245/0.621 |
| rs518147 (−697) | C | 0.349 | 0.389/0.326 | 0.774/0.379 | 0.387/0.329 | 0.623/0.43 | 0.397/0.327 | 0.834/0.361 |
| rs6318 (Cys23Ser) | Ser carrier | 0.305 | 0.293/0.261 | 0.231/0.631 | 0.33/0.215 | 2.89/0.089 | 0.377/0.183 | 8.122/0.004 |
| rs3813929-rs518147 | C-C | 0.22 | 0.238/0.169 | 1.195/0.274 | 0.259/0.141 | 3.302/0.069 | 0.203/0.157 | 0.520/0.471 |
| rs518147-rs6318 | C-Ser | 0.194 | 0.214/0.159 | 0.863/0.353 | 0.239/0.127 | 3.539/0.060 | 0.222/0.13 | 2.378/0.123 |
| rs3813929-rs6318 | C-Ser | 0.294 | 0.284/0.256 | 0.160/0.689 | 0.314/0.211 | 2.093/0.148 | 0.35/0.171 | 6.248/0.0124 |
| rs3813929-rs518147-rs6318 | C-C-Ser | 0.187 | 0.206/0.157 | 0.737/0.391 | 0.231/0.126 | 3.181/0.075 | 0.203/0.128 | 1.629/0.202 |

Since we have a relatively lower case number and unphased genotype data for females, it is not possible to reach a conclusion for individual SNP association and haplotype association in females. Subsequent ANCOVA test on Δ change or % change (data not shown) in symptom improvement after controlling for race, drugs, and the corresponding baseline psychopathology indicated that Ser carriers had a significant improvement in positive and negative symptoms (p=0.025 and 0.019, respectively) after 6 month treatment in the male patients. (See Table 7).

TABLE 7

ANCOVA test on the association between HTR2C SNPs with absolute change (Δ) in symptom improvement with gene polymorphism as the independent variable and race and corresponding baseline psychopathology as the covariates in a general linear model.

| | SNP ID | | | | |
| --- | --- | --- | --- | --- | --- |
| Male only | rs3813929 | | | | rs518147 |
| Genotype | T/T | C/C | F/P[&] | C/C | C/G |
| Counts | 17 | 95 | | 39 | NA |
| Frequency | 0.140 | 0.860 | | 0.342 | NA |
| Total_6Mon | −8.47 ± 13.25 | −7.06 ± 12.08 | 0.748/0.389[#] | −10.36 ± 11.62 | NA |
| Total_6Wk | −7.00 ± 8.23 | −5.63 ± 11.92 | 3.93/0.05[#] | −8.25 ± 11.13 | |
| Positive 4 items_6Mon | −2.06 ± 4.66 | −2.65 ± 5.75 | 0.01/0.914[#] | −3.56 ± 4.77 | NA |
| Positive 4 items_6Wk | −2.76 ± 4.66 | −2.03 ± 5.27 | 1.99/0.161 | −2.83 ± 4.60 | |
| Positive 3 items_6Mon | −1.35 ± 4.36 | −2.25 ± 4.77 | 0.04/0.835 | −2.97 ± 4.33 | NA |
| Positive 3 items_6Wk | −2.24 ± 4.31 | −1.61 ± 4.23 | 1.81/0.181 | −2.33 ± 4.10 | |
| Negative 3 items_6Mon | −0.41 ± 3.87 | −0.85 ± 2.75 | 0.15/0.700 | −1.25 ± 3.62 | NA |
| Negative 3 items_6WK | 0.00 ± 2.78 | −0.15 ± 2.84 | 0.14/0.708 | −0.03 ± 2.36 | |

| | SNP ID | | | | |
| --- | --- | --- | --- | --- | --- |
| Male only | rs518147 | | rs6318 | | |
| Genotype | G/G | F/P | Cys/Ser + Ser/Ser | Cys/Cys | F/P |
| Counts | 73 | | 24 | 89 | |
| Frequency | 0.658 | | 0.217 | 0.783 | |
| Total_6Mon | −5.64 ± 12.30 | 1.30/0.256 | −12.65 ± 9.09 | −6.18 ± 12.60 | 2.82/0.096 |
| Total_6Wk | −5.39 ± 12.57 | 0.67/0.413 | −9.58 ± 11.63 | −6.20 ± 12.12 | 0.08/0.784 |
| Positive 4 items_6Mon | −2.01 ± 5.92 | 0.99/0.322 | −5.22 ± 5.04 | −2.09 ± 5.66 | 3.86/0.025 |
| Positive 4 items_6Wk | −1.77 ± 5.45 | 0.92/0.339 | −3.19 ± 4.52 | −2.03 ± 5.39 | 0.08/0.772 |
| Positive 3 items_6Mon | −1.61 ± 4.86 | 0.82/0.367 | −4.74 ± 4.26 | −1.59 ± 4.77 | 5.19/0.025 |
| Positive 3 items_6Wk | −1.36 ± 4.28 | 1.08/0.302 | −2.62 ± 3.97 | −1.59 ± 4.37 | 0.14/0.705 |
| Negative 3 items_6Mon | −0.52 ± 2.51 | 2.64/0.107 | −2.04 ± 2.79 | −0.52 ± 2.99 | 5.73/0.019 |
| Negative 3 items_6WK | −0.18 ± 3.05 | 0.05/0.819 | −0.54 ± 2.21 | −0.14 ± 3.06 | 0.67/0.416 |

| | SNP ID | | | | |
| --- | --- | --- | --- | --- | --- |
| Female only | rs3813929 | | | | rs518147 |
| Genotype | T/T | C/C | F/P | C/C | C/G |
| Counts | 3 | 40 | | 7 | 23 |
| Frequency | 0.068 | 0.932 | | 0.135 | 0.462 |
| Total_6Mon | −7.33 ± 8.33 | −9.81 ± 10.82 | 0.29/0.595 | −9.71 ± 14.10 | −9.88 ± 10.53 |
| Total_6Wk | −3.33 ± 3.22 | 6.68 ± 12.19 | 0.37/0.0.549[#] | −9.43 ± 7.85 | −8.32 ± 14.05 |
| Positive 4 items_6Mon | 0.33 ± 6.11 | −3.75 ± 4.10 | 1.90/0.178 | −2.43 ± 5.41 | −3.71 ± 3.62 |
| Positive 4 items_6Wk | 0.33 ± 5.77 | −2.55 ± 4.44 | 0.92/0.344 | −3.71 ± 5.74 | −2.56 ± 4.74 |
| Positive 3 items_6Mon | 0.33 ± 4.51 | −3.42 ± 3.64 | 2.00/0.168 | −2.14 ± 5.34 | −3.00 ± 3.37 |
| Positive 3 items_6Wk | 1.00 ± 5.29 | −2.22 ± 4.04 | 1.41/0.242 | −3.00 ± 5.69 | −1.78 ± 4.59 |
| Negative 3 items_6Mon | −1.67 ± 3.06 | −0.59 ± 2.45 | 0.73/0.400 | −1.57 ± 5.53 | −0.53 ± 2.40 |
| Negative 3 items_6WK | 1.33 ± 2.31 | −0.93 ± 2.62 | 2.03/0.162 | 0.14 ± 2.91 | −1.00 ± 2.68 |

| | SNP ID | | | | |
| --- | --- | --- | --- | --- | --- |
| Female only | rs518147 | | rs6318 | | |
| Genotype | G/G | F/P | Cys/Ser + Ser/Ser | Cys/Cys | F/P |
| Counts | 21 | | 20 | 34 | |
| Frequency | 0.404 | | 0.382 | 0.618 | |
| Total_6Mon | −11.17 ± 11.15 | 0.22/0.802 | −10.31 ± 13.28 | −11.45 ± 9.93 | 0.06/0.811 |
| Total_6Wk | −7.76 ± 11.84 | 0.24/0.788 | −9.73 ± 12.97 | −8.00 ± 12.20 | 0.22/0.641 |
| Positive 4 items_6Mon | −4.33 ± 4.83 | 0.74/0.483 | −3.31 ± 3.61 | −4.10 ± 4.64 | 0.44/0.512[#] |
| Positive 4 items_6Wk | −2.76 ± 4.00 | 0.70/0.502 | −3.41 ± 4.35 | −2.56 ± 4.47 | 0.45/0.506 |
| Positive 3 items_6Mon | −4.06 ± 4.15 | 1.19/0.315 | −2.53 ± 3.74 | −3.59 ± 4.06 | 1.05/0.311[#] |
| Positive 3 items_6Wk | −2.71 ± 3.24 | 1.03/0.366 | −2.55 ± 4.19 | −2.24 ± 4.01 | 0.11/0.739 |

TABLE 7-continued

ANCOVA test on the association between HTR2C SNPs with absolute change (Δ) in symptom improvement with gene polymorphism as the independent variable and race and corresponding baseline psychopathology as the covariates in a general linear model.

| | | | | | |
|---|---|---|---|---|---|
| Negative 3 items_6Mon | −0.61 ± 3.15 | 0.81/0.454 | −1.75 ± 4.09 | −0.38 ± 2.90 | 2.46/0.124 |
| Negative 3 items_6WK | −1.14 ± 2.83 | 0.49/0.617 | −1.45 ± 2.86 | −0.62 ± 2.78 | 2.26/0.139 |

Clinical assessment was performed at 6 week and 6 month.
Data was presented as Mean ± SD of Δ change from baseline score.
&represents F statistic and p value calculated from ANCOVA;
represents the result from Levene's test of equality of error variances with $p < 0.05$, which against the null hypothesis that the error variance of the dependent variable is equal across groups, suggesting ANCOVA assuming homogeneity of variance is rejected.

These analyses suggest that HTR2C could be relevant to response to APDs for many types of psychopathology. Neither -759C/T nor -697G/C alone were significantly associated with symptom improvement.

meta-analysis is detailed in the Supplemental Information presented below. Six studies from Table 8, including ours, with accessible genotyping data for rs6318 and binary outcome for symptom improvement, were included.

TABLE 8

Previous association studies of HTR2C polymorphisms with treatment response to antipsychotics, mainly clozapine, in Schizophrenia.

| Reference | No. of Subjects (Male/Female) | Antipsychotics | Ethnicity | Study duration | Genetic Variants | Responder/Non-Responder |
|---|---|---|---|---|---|---|
| Sodhi M S* (1995) | 162 (unclear) | Clozapine only | Caucasian | 3 months | rs6318 | 103/59 |
| Masellis M* (1998) | 185 (132/53) | Clozapine only | Caucasian/African-American | 6 months | rs6318 | 72/67 for Caucasian; 20/19 for Afrian Americans |
| Arranz M J (2000) | 200 (unclear) | Clozapine only | Caucasian | 3 months | −330(GT)/−244(CT); rs6318 | 133/67 |
| Reynolds G P (2005) | 117 (58/59) | Chlorpromazine (56.4%); risperidone (36.8%); clozapine (3.4%); fluphenazine (2.6%); sulpiride (1%) | Chinese (Han) | 2.5 months | rs3813929 | 86/90 |
| Ikeda M (2008) | 120 (58/62) | Risperidone only | Japanese | 2.5 months | rs3813929; rs518147 | not available |
| Need A C (2009) | 524 (CATIE Phase 1) | olanzapine, perphenazine, quetiapine, risperidone and ziprasidone | Caucasian/African-American | Variable (up to 18 months) | 30 tag SNPs in HTR2C | not available |
| Liu B-C (2010) | 130 (45/85) | Risperidone only | Chinese (Han) | 2 months | rs3813929; rs518147; rs1023574; rs9698290; rs6318 | not available |
| Vehof J* (2012) | 329 (260/69); actual number is 293 (-/-) for rs3813929 and 297 for rs6318. | Clozapine (9.1%); Olanzapine (24.3%); Risperidone (22.8%); Quetiapine (5.5%); Haloperidol (7.3%); Multiple (11.2%); Aripiprazole (1.5%); others (6.7%) | Caucasian | variable | rs3813929; rs6318 | 247/82 |
| Malhotra A K* (1996) | 66 (49/17) | Clozapine only | Caucasian | 2.5 months | rs6318 | 18/48 |
| Rietschel M* (1997) | 152 (76/76) | Clozapine only | Caucasian | variable (Avg = 2.0 months) | rs6318 | 110/42 |
| Li & Meltzer* (2014) | 171 (115/56) | Clozapine (78%); Olanzapine (2.1%); Risperidone (3.8%); Melperone (7.0%); Others (9.0%) | Caucasian/African-American | 6 weeks & 6 months | rs3813929; rs518147; rs6318 | 75/63 (positive symptom at 6 month) |

*represents studies included in the meta-analysis

Meta-Analysis

In order to review and elucidate the general relationship between HTR2C polymorphisms and drug response to clozapine, a Pubmed search was conducted using Medline databases from 1966 to February, 2014. The procedure for meta-analysis is detailed in the Supplemental Information presented below. Six studies from Table 8, including ours, with accessible genotyping data for rs6318 and binary outcome for symptom improvement, were included.

Due to insignificant heterogeneity between studies (Cochran's Q=6.03, p=0.30; $I^2$=0.17 (95% CI, 0.00 to 0.62), we report the overall odds ratio with the fixed effect model is 2.00 (95% CI, 1.38-2.91, p=0.0003) and that with the random effect model is 1.94 (95% CI, 1.27-2.99, p=0.0024).

Figure 2:
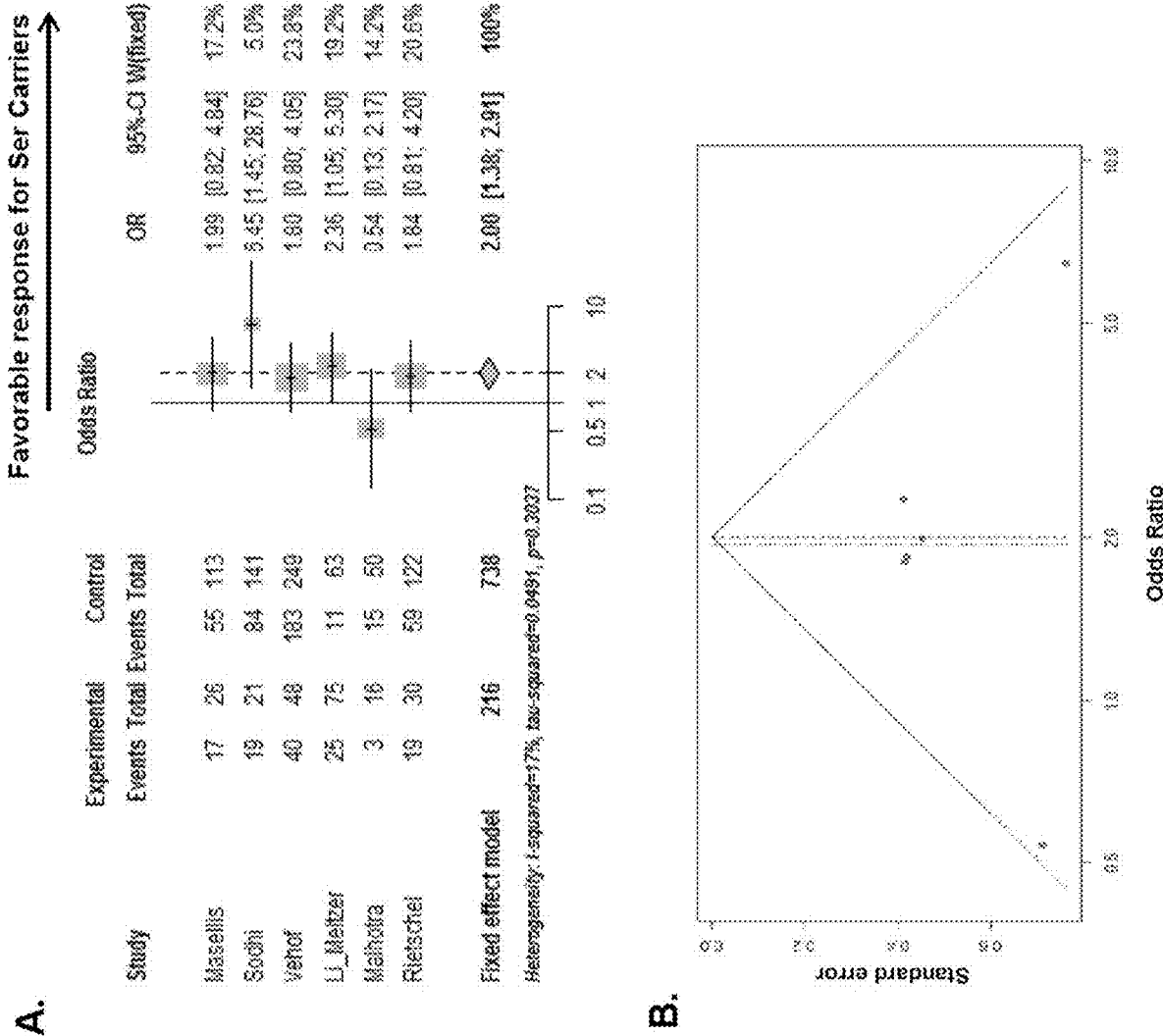
FIG. 2. A meta-analysis of the Ser carrier for rs6318 (Cys23Ser) associated with treatment response (binary data) across six studies on Caucasian samples. A. Forest Plot. Experimental=Ser carrier; Control=Non-Ser carrier; Events=number of Responder; Total=number of subjects with that genotype. The squares represent odds ratio to have a favorable treatment response if it is over 1 and the horizontal lines show the 95% confidence intervals of the corresponding odds ratio. For Vehof's study, the raw data was computed based on published improvement/no improvement ratio, genotyping data, and odds ratio. B Funnel Plot is used to assesses publication bias in meta-analysis datasets. If all studies come from a single population then the plot should look like a funnel with the diameter of the funnel decreasing as the sample size increases. In the absence of publication bias, one should expect a symmetrical funnel plot.

(See FIG. 2). QUANTO 1.2 was used to calculate the power of the test. The mode of inheritance for rs6318 was dominant. Kp=0.30 (population risk) since the prevalence of treatment responders to clozapine in the schizophrenia population is ~30%. The Ser carriers were found to have a frequency of 0.15 to 0.45 according to Table 9.

TABLE 9

Allele frequency of mainly validated HTR2C SNPs from East Asian (ASN), European (EUR), and African (AFK) population in 1000 Genome project.

| Gender | SNP ID | ASN (CHB, JPT, CHS) | EUR (CEU, TSI, FIN, GBR, IBS) | AFK (YRI, LWK, ASW) |
|---|---|---|---|---|
| Male | rs3813929 | 16.7% | 18.0% | 3.5% |
| | rs518147 | 18.1% | 37.1% | 43.5% |
| | rs6318 | 1.4% | 18.0% | 47.0% |
| Female | rs3813929 | 13.7% | 14.9% | 1.9% |
| | rs518147 | 15.1% | 31.1% | 34.0% |
| | rs6318 | 1.1% | 14.7% | 37.8% |

Allele frequency of mainly validated HTR2C SNPs from East Asian (ASN), European (EUR), and African (AFK) population in 1000Genome project. Original genotype data are retrieved from 1000 Genome database at its website.

If Ser carriers increases the odds of having treatment response by 2.0, and 216 responders and 738 non responders were genotyped, the power (chance) to detect an association with significance p<0.01 was over 90%.

DISCUSSION

We summarize the published association studies between HTR2C genetic variants and treatment response for APDs in schizophrenic patients in Table 2. There is no consistent result across all the studies; however, some potential replicable finding can be extracted. For example, the following replication studies[44,56] to Sodhi' [38] show no statistical significance, but the individual p value is close to 0.05 and does reveal a trend for association (Masellis, p=0.18 and Vehof, p=0.13). Our meta-analysis on six original studies [38,44-46,56] suggests that HTR2C Cys23Ser is associated with symptom improvement after treatment with clozapine. This is an extension of a previously reported meta-analysis on this topic[57]. Studies of a single APD (or of one dominant) are more likely to reach a positive finding than studies based on diverse treatments. APDs may have distinct effect on HTR2C, and other receptors, leading to differential degree of symptom improvement. However, our findings could also mean that the results reported here do generalize, at least, to the drugs studies here or the entire class of serotonin-dopamine receptor antagonists, of which clozapine is the prototype. One of its strengths in this study is that the majority of the patients were unmedicated at the time of assessment, providing data on the basal level of psychopathology not affected by drug treatment. Only the perspective treatment, mainly association with the clozapine was responsible for the symptom improvement.

A likely explanation for the inconsistent results among pharmacogenetic studies of clozapine response is the heterogeneity in definition and characterization of phenotype or endophenotype, the magnitude of improvement evaluated with different scale system including PANSS[58], BPRS [59], CGI-I[60], et al, some with relative small range of response outcomes, frequency of genetic variants in distinct ethnical groups, different subtypes of APDs which may or may not related to HTR2C pharmacology, the time of assessment for treatment response based on personal clinical experience, and statistical methods (dominant, recessive or others, chi-square or regression model with covariates). Patients who do not respond well are less likely to continue an antipsychotic and will eventually drop out or switch to another APD. This would favor negative results.

Another possible explanation for discrepant findings is that HTR2C may exert different or even opposite activities in the brain depending on other genetic factor[61], which are relevant to the specific neuropsychiatric disease or specific phenotype/endophenotype. Numerous studies using GWAS or candidate gene suggest the genetic mutations from multiple genes may account for the association with the trait. Therefore, to analyze multiple functional polymorphisms together, instead of individually, may lead to a better understanding of the genetic burden on the phenotype and avoid discrepant findings in association studies of individual SNP association. Despite -759C-Ser may show some additive effect on this backbone (Cys23 Ser) association, this study, including the result of the meta-analysis, strongly indicated that rs6318, but not promoter polymorphisms, is the major genetic contributor in modulating symptom improvement to clozapine. However for APD induced weight gain, the consistent finding is -759C/T associated with APD-induced weight gain[24,61].

The drug target for symptom improvement (or treatment response) in schizophrenia mainly involved Cys23 Ser. Some in vitro functional studies may partially give an explanation. Okada[40] reported functional differences between the two alleles of rs6318 by comparing their receptor-binding profiles and ability to mobilize calcium in COS-7 cells and by comparing their constitutive activities using a novel procedure for in situ reconstitution. Ser23 receptor displayed constitutively more activity than Cys23. Thus, it appears to be an abundant candidate allele capable of directly influencing inter-individual variation in behavior, susceptibility to mental disorder, and response to drug treatment including atypical antipsychotic and some antidepressant drugs that are potent HTR2C inverse agonists or antagonists. A recent study [41] further reported that despite prolonged pre-exposure to serotonin causing equally rapid and strong desensitization of both isoreceptors, a greater cell surface expression and more rapid resensitization followed by SB206553, a mixed antagonist for HTR2B and HTR2C, in Ser-receptors was observed and might be therapeutically relevant for drugs exhibiting inverse agonist properties at HTR2C. It may be concluded that prolonged exposure of both HTR2C isoreceptors to an inverse agonist increases receptor responsiveness to endogenous serotonin or other HTR2C agonists. This enhanced responsiveness occurs earlier in cells (and presumably also in individuals) expressing Ser than in those expression Cys.

Whether in vitro findings can be transferable to intact nervous system is still debatable. Mickey et al. reported that dopaminergic circuitry is more sensitive to pain stress in Ser23 carriers during a PET scan with a displaceable D2/D3 receptor radiotracer[62]. Greater dopamine release in the nucleus accumbens, caudate nucleus, and putamen was observed in the Ser23 carriers during pain, suggesting mesoaccumbal stress sensitivity may mediate the effects of HTR2C variation on the risk of neuropsychiatric disorders.

Another explanation for the discrepancies of HTR2C association with symptom improvement is mRNA editing [61]. This may help to explain why some functional variants play more important role in antipsychotic-induced weight gain but others may be more relevant to treatment response. HTR2C receptors are subject to an extraordinary degree of region-specific RNA editing. This leads to multiple receptor isoforms with dramatically different constitutive activity, expression patterns, and efficacy of APDs[63-65]. Altered editing patterns of the HTR2C receptor has been observed in the prefrontal cortex of suicide victims in a gender-specific pattern[65,66]. There is conflicting evidence for reduced RNA editing, leading to increased expression of the unedited form of HTR2C in schizophrenic patients[67]. Further study is needed to determine that HTR2C RNA editing may be involved in the maintenance of appropriate serotonergic neurotransmission and influence treatment response in psychiatric disorders. Some limited negative findings have been reported on the relationship between -759C/T or Cys23Ser and RNA editing level in brain[68,69]. Although it is still unclear whether HTR2C polymorphisms have any impact on the region-specific RNA editing, the present results warrant future studies addressing the mechanisms by which the HTR2C polymorphisms, either alone or in conjunction with other markers, as well as post-transcriptional modification, are implicated in specific features of schizophrenia, such as positive/negative symptoms, and the therapeutic effect of APDs. More studies are needed to elucidate the role of HTR2C genetic polymorphisms in treatment response with regard to specific types of symptom improvement in different ethnic population, well-balanced gender (analyzed separately), larger sample size, and single APD or APDs with similar pharmacology.

Supplemental Information
Clinical Evaluation of Treatment Response

The majority of these patients were initially hospitalized for an acute exacerbation of symptoms or because of failure to respond adequately to conventional or atypical antipsychotic drugs between 1995 and 2010, leading to 118 patients (69%) with initial diagnosis of treatment-resistant schizophrenia (TRS) as defined by Kane, et al[48]. Demographic information is provided in Table 1A and Table 1B separated by gender. Over 75% of patients were not medicated or had a drug free period of 3-10 days prior to baseline assessment. Patients were interviewed by trained raters using the Schedule for Affective Disorders and Schizophrenia[70] to establish diagnosis. This was integrated with all available data to make the final diagnosis by consensus according to the Diagnostic and Statistical Manual of Mental Disorders, third edition (DSM-III) criteria at discharge. A review of these diagnoses indicates all patients meet DSM-IV criteria for schizophrenia or schizoaffective disorder. For the purpose of this report, data from patients with either diagnosis are combined. Brief Psychiatric Rating Scale (BPRS; items rated 0-6)[59] was used to assess the severity of psychopathology. BPRS positive symptom subscale includes suspiciousness, hallucinatory behavior, unusual thought content, and conceptual disorganization. In a factor analysis of BPRS ratings in 572 schizophrenia patient, including the subjects in this study, conceptual disorganization did not cluster with suspiciousness, hallucinatory behavior, and unusual thought content (Jayathilake et al unpublished data). Similar findings have been reported by others [71], suggesting conceptual disorganization is weakly connected to the positive symptom domain. We, therefore, excluded conceptual disorganization in the analyses of positive symptoms which follow. The remaining three items, suspiciousness, hallucinatory behavior, and unusual thought content are referred to as the positive 3-item. BPRS negative subscale is comprised of three items: emotional withdrawal, motor retardation and blunted affect. The anxiety-depression subscale consists of three items as well: anxiety, guilty feelings, and depressive mood. Categorical treatment response was evaluated at 6 week and 6 months, using the criteria based upon Kane et al. [48]. A reduction of >20% in BPRS total or subscale scores was considered as responder. In cases where patients were very close to the operational criteria for response (>15% or <25%), a reduction of at least one category on the Clinical Global Impressions (CGI) scale was considered in order to enhance the definition of response.

After a description of the study, written informed consent was obtained from every subject. All patients provided written informed consent to remain drug free during the assessment. The drug free period was terminated if patient well-being required it.

Some were not receiving psychotropic drugs prior to admission because of non-compliance. The study protocol was approved by institutional ethics committees and was performed in accordance with the ethical standards laid down in the 1964 Declaration of Helsinki.

Meta-Analysis

In order to review and elucidate the general relationship between HTR2C polymorphisms and drug response to clozapine, a Pubmed search was conducted using Medline databases from 1966 to February, 2014. The following combination of search terms, "antipsychotic agents"[MeSH Terms] AND 5-HTR2C[All Fields] OR HTR2C[All Fields] AND "humans" [MeSH Terms], help to identified 217 abstracts.

There are 11 English-language citations which were extracted because of the topic on drug response in schizophrenia with reported genotype data on HTR2C polymorphisms. The references listed from obtained articles were also searched to identify further relevant citations. There was a lack of study of rs6318 in East Asian population and rs3813929 in African-American population due to very low MAF (<5%, Table 9). As showed in Table 2, the following information was collected from these papers: names of first authors with year of publication, number of subject (separated by gender), percentage of patients on clozapine or other APDs, ethnicity (European, African-American, East Asian), study duration, observed genetic variants in HTR2C, Phenotype observed (binary and/or quantitative), Responder/No responder Ratio, Statistical analysis, and summary of the results.

Those full-text articles were then scrutinized by two authors, J Li and HY Meltzer, to determine eligibility for inclusion in the meta-analysis. Only rs6318 for which more than two studies have been published. Finally, six studies, including ours, with accessible genotyping data for rs6318 and binary outcome for symptom improvement, were included. We did not stratify the patients for each study based on the gender or ethnicity. Only two studies (ours and Masellis') recruited a small portion of African-American subjects. This is an extension of a previously reported meta-analysis on the same topic[57]. Although over 50% of the subjects received clozapine or olanzapine treatment in each study except Vehof's, the definition of drug responder varied. We did not include a candidate-gene study of SNP array data generated from the CATIE sample[72] because clozapine was not the observed APD and the trait for treatment response is quantitative but not binary (Table 2). There is no significant deviation from HWE (p>0.001) for rs6318 in each studies. In order to reduce the heterogeneity among these studies and avoid the publication bias, we included all patients (male and female) and only improvement in positive symptoms was considered in our study in order to match another study [56]. Heterogeneity among the studies was assessed by means of the $I^2$ inconsistency test and Cochran's Q statistics under a null hypothesis test in which p<0.05.

| | OR | 95%-CI | z | p.value |
|---|---|---|---|---|
| | Number of studies combined: k = 6 | | | |
| Fixed effect model | 2.0038 | [1.3801; 29093] | 3.6535 | 0.0003 |
| Random effects model | 1.9437 | [1.2655; 2.9851] | 3.0357 | 0.0024 |

Quantifying Heterogeneity:
  Tau^2=0.0491; H=1.1 [1; 1.62]; I^2=17% [0%; 61.8%]
Test of Heterogeneity:
  Q d.f. p.value
  6.03 5 0.3037

REFERENCES

1. Barnes N M, Sharp T (1999) A review of central 5-H T receptors and their function. Neuropharmacology 38: 1083-1152.
2. Berg K A, Clarke W P, Cunningham K A, Spampinato U (2008) Fine-tuning serotonin2c receptor function in the brain: molecular and functional implications. Neuropharmacology 55: 969-976.
3. Giorgetti M, Tecott L H (2004) Contributions of 5-H T(2C) receptors to multiple actions of central serotonin systems. Eur J Pharmacol 488: 1-9.
4. Di Giovanni G, De Deurwaerdere P, Di Mascio M, Di Matteo V, Esposito E, et al. (1999) Selective blockade of serotonin-2C/2B receptors enhances mesolimbic and mesostriatal dopaminergic function: a combined in vivo electrophysiological and microdialysis study. Neuroscience 91: 587-597.
5. Marquis K L, Sabb A L, Logue S F, Brennan J A, Piesla M J, et al. (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. J Pharmacol Exp Ther 320: 486-496.
6. Boothman L, Raley J, Denk F, Hirani E, Sharp T (2006) In vivo evidence that 5-HT(2C) receptors inhibit 5-H T neuronal activity via a GABAergic mechanism. Br J Pharmacol 149: 861-869.
7. Calcagno E, Carli M, Baviera M, Invernizzi R W (2009) Endogenous serotonin and serotonin2C receptors are involved in the ability of M100907 to suppress cortical glutamate release induced by NMDA receptor blockade. J Neurochem 108: 521-532.
8. Labasque M, Reiter E, Becamel C, Bockaert J, Marin P (2008) Physical interaction of calmodulin with the 5-hydroxytryptamine2C receptor C-terminus is essential for G protein-independent, arrestin-dependent receptor signaling. Mol Biol Cell 19: 4640-4650.
9. Gavarini S, Becamel C, Altier C, Lory P, Poncet J, et al. (2006) Opposite effects of PSD-95 and MPP3 PDZ proteins on serotonin 5-hydroxytryptamine2C receptor desensitization and membrane stability. Mol Biol Cell 17: 4619-4631.
10. Hsueh Y P (2006) The role of the MAGUK protein CASK in neural development and synaptic function. Curr Med Chem 13: 1915-1927.
11. Jentsch J D, Roth R H (1999) The neuropsychopharmacology of phencyclidine: from NMDA receptor hypofunction to the dopamine hypothesis of schizophrenia. Neuropsychopharmacology 20: 201-225.
12. Lisman J E, Coyle J T, Green R W, Javitt D C, Benes F M, et al. (2008) Circuit-based framework for understanding neurotransmitter and risk gene interactions in schizophrenia. Trends Neurosci 31: 234-242.
13. Rushlow W J, Seah C, Sutton L P, Bjelica A, Rajakumar N (2009) Antipsychotics affect multiple calcium calmodulin dependent proteins. Neuroscience 161: 877-886.
14. Rauser L, Savage J E, Meltzer H Y, Roth B L (2001) Inverse agonist actions of typical and atypical antipsychotic drugs at the human 5-hydroxytryptamine(2C) receptor. J Pharmacol Exp Ther 299: 83-89.
15. Kroeze W K, Hufeisen S J, Popadak B A, Renock S M, Steinberg S, et al. (2003) H1-histamine receptor affinity predicts short-term weight gain for typical and atypical antipsychotic drugs. Neuropsychopharmacology 28: 519-526.
16. Meltzer H Y, Li Z, Kaneda Y, Ichikawa J (2003) Serotonin receptors: their key role in drugs to treat schizophrenia. Prog Neuropsychopharmacol Biol Psychiatry 27: 1159-1172.
17. Meltzer H Y, Huang M (2008) In vivo actions of atypical antipsychotic drug on serotonergic and dopaminergic systems. Prog Brain Res 172: 177-197.
18. Abi-Dargham A, van de Giessen E, Slifstein M, Kegeles L S, Laruelle M (2009) Baseline and amphetamine-stimulated dopamine activity are related in drug-naive schizophrenic subjects. Biol Psychiatry 65: 1091-1093.
19. Laruelle M (1998) Imaging dopamine transmission in schizophrenia. A review and meta-analysis. Q J Nucl Med 42: 211-221.
20. Dunlop J, Watts S W, Barrett J E, Coupet J, Harrison B, et al. (2011) Characterization of vabicaserin (SCA-136), a selective 5-hydroxytryptamine 2C receptor agonist. J Pharmacol Exp Ther 337: 673-680.
21. Castensson A, Emilsson L, Sundberg R, Jazin E (2003) Decrease of serotonin receptor 2C in schizophrenia brains identified by high-resolution mRNA expression analysis. Biol Psychiatry 54: 1212-1221.
22. Iwamoto K, Kakiuchi C, Bundo M, Ikeda K, Kato T (2004) Molecular characterization of bipolar disorder by comparing gene expression profiles of postmortem brains of major mental disorders. Mol Psychiatry 9: 406-416.
23. Hernando-Herraez I, Prado-Martinez J, Garg P, Fernandez-Callejo M, Heyn H, et al. (2013) Dynamics of DNA methylation in recent human and great ape evolution. PLoS Genet 9: e1003763.
24. De Luca V, Muller D J, Hwang R, Lieberman J A, Volavka J, et al. (2007) HTR2C haplotypes and antipsychotics-induced weight gain: X-linked multimarker analysis. Hum Psychopharmacol 22: 463-467.
25. Reynolds G P, Yao Z, Zhang X, Sun J, Zhang Z (2005) Pharmacogenetics of treatment in first-episode schizophrenia: D3 and 5-HT2C receptor polymorphisms separately associate with positive and negative symptom response. Eur Neuropsychopharmacol 15: 143-151.
26. Liu B C, Zhang J, Wang L, Li W, Wang Y, et al. (2010) HTR2C promoter polymorphisms are associated with risperidone efficacy in Chinese female patients. Pharmacogenomics 11: 685-692.
27. Hu X, Giotakis O, Li T, Karwautz A, Treasure J, et al. (2003) Association of the 5-HT2c gene with susceptibility and minimum body mass index in anorexia nervosa. Neuroreport 14: 781-783.
28. Lerer B, Macciardi F, Segman R H, Adolfsson R, Blackwood D, et al. (2001) Variability of 5-HT2C receptor cys23ser polymorphism among European populations and vulnerability to affective disorder. Mol Psychiatry 6: 579-585.

29. Gutierrez B, Fananas L, Arranz M J, Valles V, Guillamat R, et al. (1996) Allelic association analysis of the 5-HT2C receptor gene in bipolar affective disorder. Neurosci Lett 212: 65-67.
30. Brummett B H, Babyak M A, Jiang R, Shah S H, Becker R C, et al. (2013) A functional polymorphism in the 5HTR2C gene associated with stress responses also predicts incident cardiovascular events. PLoS One 8: e82781.
31. Murad I, Kremer I, Dobrusin M, Muhaheed M, Bannoura I, et al. (2001) A family-based study of the Cys23Ser 5HT2C serotonin receptor polymorphism in schizophrenia. Am J Med Genet 105: 236-238.
32. Holmes C, Arranz M J, Powell J F, Collier D A, Lovestone S (1998) 5-HT2A and 5-HT2C receptor polymorphisms and psychopathology in late onset Alzheimer's disease. Hum Mol Genet 7: 1507-1509.
33. Assal F, Alarcon M, Solomon E C, Masterman D, Geschwind D H, et al. (2004) Association of the serotonin transporter and receptor gene polymorphisms in neuropsychiatric symptoms in Alzheimer disease. Arch Neurol 61: 1249-1253.
34. Pritchard A L, Harris J, Pritchard C W, Coates J, Haque S, et al. (2008) Role of 5H T 2A and 5H T 2C polymorphisms in behavioural and psychological symptoms of Alzheimer's disease. Neurobiol Aging 29: 341-347.
35. Segman R H, Ebstein R P, Heresco-Levy U, Gorfine M, Avnon M, et al. (1997) Schizophrenia, chronic hospitalization and the 5-HT2C receptor gene. Psychiatr Genet 7: 75-78.
36. Gunes A, Dahl M L, Spina E, Scordo M G (2008) Further evidence for the association between 5-HT2C receptor gene polymorphisms and extrapyramidal side effects in male schizophrenic patients. Eur J Clin Pharmacol 64: 477-482.
37. Kusumi M, Araki H, Ijiri T, Kowa H, Adachi Y, et al. (2004) Serotonin 2C receptor gene Cys23Ser polymorphism: a candidate genetic risk factor of migraine with aura in Japanese population. Acta Neurol Scand 109: 407-409.
38. Sodhi M S, Arranz M J, Curtis D, Ball D M, Sham P, et al. (1995) Association between clozapine response and allelic variation in the 5-HT2C receptor gene. Neuroreport 7: 169-172.
39. Arranz M J, Munro J, Birkett J, Bolonna A, Mancama D, et al. (2000) Pharmacogenetic prediction of clozapine response. Lancet 355: 1615-1616.
40. Okada M, Northup J K, Ozaki N, Russell J T, Linnoila M, et al. (2004) Modification of human 5-HT(2C) receptor function by Cys23Ser, an abundant, naturally occurring amino-acid substitution. Mol Psychiatry 9: 55-64.
41. Walstab J, Steinhagen F, Bruss M, Gothert M, Bonisch H (2011) Differences between human wild-type and C23S variant 5-HT2C receptors in inverse agonist-induced resensitization. Pharmacol Rep 63: 45-53.
42. Lappalainen J, Zhang L, Dean M, Oz M, Ozaki N, et al. (1995) Identification, expression, and pharmacology of a Cys23-Ser23 substitution in the human 5-HT2c receptor gene (HTR2C). Genomics 27: 274-279.
43. Fentress H M, Grinde E, Mazurkiewicz J E, Backstrom J R, Herrick-Davis K, et al. (2005) Pharmacological properties of the Cys23Ser single nucleotide polymorphism in human 5-HT2C receptor isoforms. Pharmacogenomics J 5: 244-254.
44. Masellis M, Basile V, Meltzer H Y, Lieberman J A, Sevy S, et al. (1998) Serotonin subtype 2 receptor genes and clinical response to clozapine in schizophrenia patients. Neuropsychopharmacology 19: 123-132.
45. Malhotra A K, Goldman D, Ozaki N, Rooney W, Clifton A, et al. (1996) Clozapine response and the 5HT2C Cys23Ser polymorphism. Neuroreport 7: 2100-2102.
46. Rietschel M, Naber D, Fimmers R, Moller H J, Propping P, et al. (1997) Efficacy and side-effects of clozapine not associated with variation in the 5-HT2C receptor. Neuroreport 8: 1999-2003.
47. Meltzer H Y, Brennan M D, Woodward N D, Jayathilake K (2008) Association of Sult4A1 SNPs with psychopathology and cognition in patients with schizophrenia or schizoaffective disorder. Schizophr Res 106: 258-264.
48. Kane J, Honigfeld G, Singer J, Meltzer H (1988) Clozapine for the treatment-resistant schizophrenic. A double-blind comparison with chlorpromazine. Arch Gen Psychiatry 45: 789-796.
49. Colantuoni C, Lipska B K, Ye T, Hyde T M, Tao R, et al. (2011) Temporal dynamics and genetic control of transcription in the human prefrontal cortex. Nature 478: 519-523.
50. Numata S, Ye T, Hyde T M, Guitart-Navarro X, Tao R, et al. (2012) DNA methylation signatures in development and aging of the human prefrontal cortex. Am J Hum Genet 90: 260-272.
51. Covell N H, Weissman E M, Essock S M (2004) Weight gain with clozapine compared to first generation antipsychotic medications. Schizophr Bull 30: 229-240.
52. Purcell S, Neale B, Todd-Brown K, Thomas L, Ferreira M A, et al. (2007) PLINK: a tool set for whole-genome association and population-based linkage analyses. Am J Hum Genet 81: 559-575.
53. Buckland P R, Hoogendoorn B, Guy C A, Smith S K, Coleman S L, et al. (2005) Low gene expression conferred by association of an allele of the 5-HT2C receptor gene with antipsychotic-induced weight gain. Am J Psychiatry 162: 613-615.
54. Yuan X, Yamada K, Ishiyama-Shigemoto S, Koyama W, Nonaka K (2000) Identification of polymorphic loci in the promoter region of the serotonin 5-HT2C receptor gene and their association with obesity and type II diabetes. Diabetologia 43: 373-376.
55. Hill M J, Reynolds G P (2011) Functional consequences of two HTR2C polymorphisms associated with antipsychotic-induced weight gain. Pharmacogenomics 12: 727-734.
56. Vehof J, Burger H, Wilffert B, Al Hadithy A, Alizadeh B Z, et al. (2012) Clinical response to antipsychotic drug treatment: association study of polymorphisms in six candidate genes. Eur Neuropsychopharmacol 22: 625-631.
57. Kirchheiner J, Nickchen K, Bauer M, Wong M L, Licinio J, et al. (2004) Pharmacogenetics of antidepressants and antipsychotics: the contribution of allelic variations to the phenotype of drug response. Mol Psychiatry 9: 442-473.
58. Kay S R, Fiszbein A, Opler L A (1987) The positive and negative syndrome scale (PANSS) for schizophrenia. Schizophr Bull 13: 261-276.
59. Overall J E, Gorham D R (1962) The Brief Psychiatric Rating-Scale. Psychological Reports 10: 799-812.
60. Guy W (1976) ECDEU Assessment Manual for Psychopharmacology—Revised. DHEW Publ No ADM 76: 218-222.
61. Drago A, Serretti A (2009) Focus on HTR2C: A possible suggestion for genetic studies of complex disorders. Am J Med Genet B Neuropsychiatr Genet 150B: 601-637.
62. Mickey B J, Sanford B J, Love T M, Shen P H, Hodgkinson C A, et al. (2012) Striatal dopamine release 63. Burns C M, Chu H, Rueter S M, Hutchinson L K, Canton H, et al. (1997) Regulation of serotonin-2C receptor G-protein coupling by RNA editing. Nature 387: 303-308.
64. Morabito M V, Emeson R B (2009) RNA editing as a therapeutic target for CNS disorders. Neuropsychopharmacology 34: 246.
65. Niswender C M, Herrick-Davis K, Dilley G E, Meltzer H Y, Overholser J C, et al. (2001) RNA editing of the human serotonin 5-HT2C receptor. alterations in suicide and implications for serotonergic pharmacotherapy. Neuropsychopharmacology 24: 478-491.
66. Gurevich I, Tamir H, Arango V, Dwork A J, Mann J J, et al. (2002) Altered editing of serotonin 2C receptor pre-mRNA in the prefrontal cortex of depressed suicide victims. Neuron 34: 349-356.
67. Sodhi M S, Burnet P W, Makoff A J, Kerwin R W, Harrison P J (2001) RNA editing of the 5-HT(2C) receptor is reduced in schizophrenia. Mol Psychiatry 6: 373-379.
68. Iwamoto K, Bundo M, Kato T (2009) Serotonin receptor 2C and mental disorders: genetic, expression and RNA editing studies. RNA Biol 6: 248-253.
69. Bundo M, Iwamoto K, Yamada K, Yoshikawa T, Kato T (2010) Mutation screening and assessment of the effect of genetic variations on expression and RNA editing of serotonin receptor 2C in the human brain. Psychiatry Clin Neurosci 64: 57-61.
70. Endicott J, Spitzer R L (1978) A diagnostic interview: the schedule for affective disorders and schizophrenia. Arch Gen Psychiatry 35: 837-844.
71. Lindenmayer J P, Bernstein-Hyman R, Grochowski S (1994) A new five factor model of schizophrenia. Psychiatr Q 65: 299-322.
72. Need A C, Keefe R S, Ge D, Grossman I, Dickson S, et al. (2009) Pharmacogenetics of antipsychotic response in the CATIE trial: a candidate gene analysis. Eur J Hum Genet 17: 946-957.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method comprising:
   (a) receiving results of a test indicating that a nucleic acid sample from a patient comprises a combination of HTR2C polymorphic alleles comprising a polymorphic allele resulting in a Cys23Ser amino acid substitution, and a C-allele of rs3813929 (-759C/T) polymorphism; and
   (b) administering an atypical antipsychotic drug (APD) to the patient after receiving the results of the test;
   wherein the patient has exhibited negative symptoms of schizophrenia.

2. The method of claim 1, wherein the test was performed by amplifying at least a portion of the HTR2C gene from the nucleic acid sample and detecting the HTR2C polymorphisms in the amplified portion.

3. The method of claim 1, wherein the test was performed by sequencing at least a portion of the HTR2C gene from the nucleic acid sample or from an amplicon obtained by amplifying at least a portion of the HTR2C gene from the nucleic acid sample.

4. The method of claim 1, wherein the test was performed by contacting the nucleic acid comprising the HTR2C polymorphic alleles with a nucleic acid probe that hybridizes specifically to nucleic acid comprising the HTR2C polymorphic alleles.

5. The method of claim 1, wherein the test comprises determining whether the nucleic acid sample is homozygous for each of the HTR2C polymorphic alleles.

6. The method of claim 1, wherein the test comprises determining whether the nucleic acid sample is heterozygous for each of the HTR2C polymorphic alleles.

7. The method of claim 1, wherein the nucleic acid sample is obtained from blood or a blood product.

8. The method of claim 1, wherein the atypical APD comprises clozapine, olanzapine, risperidone, or serindole.

* * * * *